(12) United States Patent
Tomohira

(10) Patent No.: US 8,734,843 B2
(45) Date of Patent: May 27, 2014

(54) MEDICAMENT SUSTAINED-RELEASE PARTICLES AND METHOD FOR PREPARING THE SAME

(75) Inventor: Yuso Tomohira, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1490 days.

(21) Appl. No.: 10/561,444

(22) PCT Filed: Jun. 17, 2004

(86) PCT No.: PCT/JP2004/008824
§ 371 (c)(1),
(2), (4) Date: Dec. 20, 2005

(87) PCT Pub. No.: WO2005/000312
PCT Pub. Date: Jan. 6, 2005

(65) Prior Publication Data
US 2007/0098843 A1     May 3, 2007

(30) Foreign Application Priority Data

Jun. 27, 2003    (JP) ................................. 2003-184040

(51) Int. Cl.
  *A61K 9/14*    (2006.01)
  *A61K 9/16*    (2006.01)
  *A61K 9/22*    (2006.01)
(52) U.S. Cl.
  USPC ........................... 424/486; 424/490; 424/468
(58) Field of Classification Search
  USPC ................................. 424/457, 486, 490, 468
  See application file for complete search history.

(56) References Cited

U.S. PATENT DOCUMENTS

| | | | |
|---|---|---|---|
| 3,264,131 A | 8/1966 | Nagel | |
| 5,443,846 A | 8/1995 | Yoshioka et al. | |
| 5,593,690 A * | 1/1997 | Akiyama et al. | 424/457 |
| 5,628,993 A | 5/1997 | Yamagata et al. | |
| 6,537,671 B2 * | 3/2003 | Muthiah | 428/413 |
| 7,927,628 B2 | 4/2011 | Yuso | |
| 2002/0176888 A1 * | 11/2002 | Bartholomaeus et al. | 424/469 |
| 2004/0175422 A1 | 9/2004 | Tomohira | |

FOREIGN PATENT DOCUMENTS

| | | |
|---|---|---|
| CN | 1104488 | 7/1995 |
| EP | 0 443 572 A1 | 8/1991 |
| EP | 0 799 616 A1 | 10/1997 |
| EP | 0 841 062 A1 | 5/1998 |
| JP | 6-91150 A | 4/1994 |
| JP | 6-47531 | 6/1994 |
| JP | 6-47531 B | 6/1994 |
| JP | 8-505841 | 6/1996 |
| JP | 2893191 | 3/1999 |
| JP | 2915590 | 4/1999 |
| JP | 11-171775 | 6/1999 |
| JP | 6-3124063 | 10/2000 |
| JP | 3130058 B2 | 1/2001 |
| JP | 2001-106627 | 4/2001 |
| JP | 2002-226304 | 5/2002 |
| JP | 2002-179571 | 6/2002 |
| JP | 2003-040764 | 2/2003 |
| JP | 2003-40764 A | 2/2003 |
| WO | 97/03656 | 2/1997 |
| WO | 02/096466 A1 | 12/2002 |
| WO | 03/070223 A1 | 8/2003 |

OTHER PUBLICATIONS

Kojima et al., Development of controlled release matrix pellets by annealing with micronized water-insoluble or enteric polymers, Journal of Controlled Release, 2002, 82, pp. 335-343.*
Lab Mixer uses production principles, British Plastic and Rubber, 2001, www.highbeam.com/doc/1G1-70912144.html.*
Lochtec ApS, www.lochtec.dk/Produkter/Lab/lab.html.*
The Japanese Pharmacopoeia, $14^{th}$ Edition, Dissolution Test ($2^{nd}$ Method, Paddle Method), B-680 (2001).
Kouteisho, "Yushirui Shiken Hou" (The Japanese Standards for Food Additives, "Testing Methods for Fats and Oils"), Hirokawa Shoten, B-195 (1999).
Office Action issued from the Korean Patent Office on Oct. 20, 2010 in a counterpart Korean Application No. 10-2005-7025130.
Y. Akiyama, et al, "Novel oral controlled-release microspheres using polyglycerol esters of fatty acids", Journal of Controlled Release, vol. 26, No. 1, Jul. 1, 1993, pp. 1-10.
Supplementary European Search Report issued on Mar. 2, 2012 from the European Patent Office in corresponding European Application No. 04 746 293.2.

* cited by examiner

*Primary Examiner* — Lezah Roberts
*Assistant Examiner* — Tracy Liu
(74) *Attorney, Agent, or Firm* — Sughrue Mion, PLLC

(57) ABSTRACT

The present invention provides theophylline sustained release particles which contain a polyglycerol fatty acid ester as a matrix base material, which have a homogenous nucleus particle structure, which can effectively mask the unpleasant taste of medicaments, and which exhibit an excellent sustained medicament releasability (dissolvability) and outstanding storage stability. In particular, the present invention provides, among other things, a method for preparing theophylline sustained release particles comprising the steps of heating a matrix base material containing a polyglycerol fatty acid ester, theophylline and ethyl cellulose to give a molten mixture; spray-cooling the molten mixture to obtain spherical core particles having an average particle diameter of 250 μm or less; and applying fine particles to the core particles by fusion coating.

12 Claims, 5 Drawing Sheets

MEDICAMENT SUSTAINED-RELEASE PARTICLES AND METHOD FOR PREPARING THE SAME

This Application is a 371 of PCT/JP2004/008824, filed Jun. 17, 2004; the disclosure of which is incorporated herein by reference.

TECHNICAL FIELD

The present invention relates to particles for sustainedly releasing a medicament, in particular, particles that sustainedly release theophylline, and a method for preparing such particles.

BACKGROUND OF THE INVENTION

To control the rate of medicament release, and to enhance storage stability and taste-masking effect, various pharmaceutical preparations have been disclosed in which low-melting-point substances (for example, polyglycerol fatty acid esters and glycerol fatty acid esters) are used as matrix base materials.

For example, Japanese Patent No. 2893191 discloses a method for obtaining spherical particles which comprises the steps of fusing a polyglycerol fatty acid-containing matrix, mixing the fused matrix with a medicament, and granulating the mixture by spray-chilling. According to this patent, due to the polyglycerol fatty acid ester, a pharmaceutical preparation with stably controlled medicament release can be prepared. The patent also discloses that by adjusting the HLB (hydrophilic-lipophilic balance) of the polyglycerol fatty acid ester, the rate of medicament release can be controlled.

Japanese Unexamined Patent Publication No. 505841/1996 discloses a drug delivery system with substantially no taste that comprises a medicament with an unpleasant taste, a low-melting-point substance and a hydrophobic polymer.

Japanese Examined Patent Publication No. 47531/1994 discloses particles with a sustained procainamide hydrochloride release prepared by adhering procainamide hydrochloride to the surface of a low-melting-point substance nucleus with heating and, while maintaining the temperature at the melting point of the low-melting-point substance or higher, and adhering talc to surface thereof. This sustained-release particulate is said to have excellent sustained release properties, appearance, strength, stability, etc.

Japanese Patent No. 3124063 discloses particles prepared by heating a granular polyglycerol fatty acid ester having a melting point of 40-80° C. and a powder to fluidize them, thereby reportedly enabling the active ingredient contained in the powder to be steadily released and rendering the active ingredient stabilized over a long period of time.

DISCLOSURE OF THE INVENTION

As a result of their own research of the pharmaceutical preparations disclosed in the aforementioned prior art publications, however, the invention found disadvantages as described hereinbelow:

(a) Japanese Patent No. 2893191 discloses a method for preparing particles of a matrix formulation, comprising the steps of heating and mixing a pharmacologically active substance and a matrix base material containing a polyglycerol fatty acid to give a molten mixture, and granulating the molten mixture by spray-chilling. In this method, it was found that when theophylline was used as the pharmacologically active substance, the resulting molten mixture showed a significantly high viscosity, thereby making uniform stirring and mixing difficult. In particular, this tendency was more pronounced when a high proportion of polyglycerol fatty acid ester was contained as the matrix base material. Therefore, it was almost impossible to prepare core particles, with theophylline being uniformly dispersed in the matrix of each core particle, and the core particles obtained did not attain a stably controlled medicament releasability (see, for example, Test Example 1).

(b) The inventors prepared core particles containing a pharmacologically active substance and a matrix base material composed of a polyglycerol fatty acid ester having a low hydrophilic-lipophilic balance (HLB) as disclosed in Japanese Patent Publication No. 2893191, and attempted to fusion-coat the core particles with a fine powder of talc or the like while heating and agitating. The inventors found that before the product temperature reached the melting point, i.e., before the core particles were coated with the fine powder, the core particles electrostatically adhered to the inner walls of a mixer/granulator, and the accumulation of the adhered core particles thickened, thereby impairing the efficiency of agitating the ingredients, decreasing thermal conductivity to the core particles, and making it difficult to completely fusion-coat the surface of the core particles with the fine powder, thereby leading to a reduced product yield (see, for example, Test Example 2).

Accordingly, a primary object of the present invention is to overcome disadvantage (a), i.e., to enhance the mixing efficiency by lowering the viscosity of a molten mixture containing a polyglycerol fatty acid ester and theophylline as well as to obtain homogenous particles of a matrix formulation having a stably controlled medicament releasability (dissolvability). Herein the phrase "stably controlled medicament releasability (dissolvability)" refers to exhibiting substantially no time dependent change in the rate of medicament release (dissolution) after the pharmaceutical preparation has been stored for a long period of time, thus retaining the property of sustained release (dissolution).

Another primary object of the present invention is to overcome disadvantage (b), i.e., when a fine powder is applied by fusion coating to core particles containing a polyglycerol fatty acid ester used as a matrix base material, to inhibit the core particles from electrostatically adhering to the inner walls of a granulator due to the matrix base material to efficiently perform the fusion coating process, and to obtain particles of a matrix formulation having a stably controlled medicament releasability (dissolvability).

The inventors conducted extensive research to overcome disadvantage (a) and found that by adding a specific amount of ethyl cellulose (hereinafter sometimes referred to as "EC") to a molten mixture of a polyglycerol fatty acid ester and theophylline, the viscosity of the molten mixture can be drastically decreased. The inventors conducted further research based on this finding and accomplished the present invention.

In particular, the present invention provides theophylline sustained release particles and methods for preparing the same (hereinafter sometimes referred to as the "first embodiment") as follows:

Item 1. A method for preparing theophylline sustained release particles comprising heating a matrix base material comprising a polyglycerol fatty acid ester, theophylline and ethyl cellulose to give a liquefied mixture; and granulating the liquefied mixture by spray-cooling.

Item 2. The method according to Item 1 comprising heating a matrix base material comprising a polyglycerol fatty acid ester, theophylline and ethyl cellulose to give a liquefied mixture;

granulating the liquefied mixture by spray-cooling to obtain spherical core particles; and applying fine powder to the core particles by fusion coating.

Item 3. The method according to Item 2, wherein the core particles have a theophylline content of about 8 to about 50 wt. % and an ethyl cellulose content of about 0.01 to about 5 wt. %, and the fine powder is applied to the core particles in an amount of about 5 to about 50 parts by weight per 100 parts by weight of the core particles.

Item 4. The method according to Item 2 or 3, wherein the core particles have an average particle diameter of 250 μm or less, and the theophylline sustained release particles obtained by fusion coating have an average particle diameter of 450 μm or less.

Item 5. The method according to any one of Items 1-4, wherein the polyglycerol fatty acid ester is a polyglycerol fatty acid half ester.

Item 6. The method according to any one of Items 1-5, wherein the polyglycerol fatty acid ester is a triglycerol behenic acid half ester.

Item 7. The method according to Item 1 or 2, wherein the matrix base material further contains a glycerol fatty acid ester.

Item 8. The method according to Item 7, wherein the glycerol fatty acid ester is at least one member selected from the group consisting of a glycerol behenic acid ester and glycerol stearic acid ester.

Item 9. The method according to Item 8, wherein the glycerol fatty acid ester is a glycerol behenic acid ester.

Item 10. The method according to any one of Items 2-9, wherein the fusion coating is performed using agitation method.

Item 11. The method according to any one of Items 2-10, wherein the fusion coating is performed at a temperature in the vicinity of the melting point or the softening point of the matrix base material.

Item 12. The method according to any one of Items 1-11, wherein the matrix base material has a hydroxyl value of about 60 or greater.

Item 13. The method according to any one of Items 2-12, wherein the fine powder is at least one member selected from the group consisting of talc, magnesium stearate, titanium oxide, ethyl cellulose, calcium stearate and cellulose acetate.

Item 14. The method for preparing theophylline sustained release particles according to Item 2 further comprising the step of heat treatment after the fusion coating.

Item 15. The method according to Item 2 further comprising subjecting the core particles to a heat treatment before the fusion coating.

Item 16. The method according to Item 14 or 15, wherein the heat treatment is conducted at a temperature from about 40° C. to about the melting point or the softening point of the matrix base material.

Item 17. Theophylline sustained release particles obtainable by the method according to any one of Items 1-16.

Item 18. Particles comprising a matrix base material containing a polyglycerol fatty acid ester, theophylline and ethyl cellulose, the theophylline and ethyl cellulose being uniformly dispersed throughout the matrix base material.

Item 19. Theophylline sustained release particles each comprising the particle of Item 18 as nucleus particle and a coating layer comprising a fine powder formed around the nucleus particle.

Item 20. The theophylline sustained release particles according to any one of Items 17-19 having a 2-hour theophylline dissolution rate of about 15 to about 55%, a 4-hour dissolution rate of about 25 to about 70% and a 6-hour dissolution rate of about 50 to about 95%, as measured according to *The Japanese Pharmacopoeia*, $14^{th}$ Edition, Dissolution Test ($2^{nd}$ Method, Paddle Method) at a stirring speed of 75 rpm using water or a 0.5% aqueous polysorbate 80 solution as test solution.

Moreover, the inventors conducted extensive research to overcome disadvantage (b) and found that by using a matrix base material having a specific hydroxyl value, the occurrence of electrostatic adhesion of core particles upon fusion coating can be inhibited. The inventors conducted further research based on this finding and accomplished the present invention.

In particular, the present invention provides medicament sustained release particles and methods for preparing them (hereinafter sometimes referred to as the "second embodiment") as follows:

Item 21. A method for preparing medicament sustained release particles comprising applying a fine powder by fusion coating to core particles containing a pharmacologically active substance and a matrix base material that has a hydroxyl value of 60 or greater and contains a polyglycerol fatty acid ester.

Item 22. The method according to Item 21 comprising heating a pharmacologically active substance and a matrix base material that has a hydroxyl value of 60 or greater and contains a polyglycerol fatty acid ester to thereby give a liquefied mixture, granulating the liquefied mixture by spray-cooling to obtain spherical core particles; and applying fine particles to the core particles by fusion coating.

Item 23. The method according to Item 21 or 22, wherein the fusion coating is performed at a temperature in the vicinity of the melting point or the softening point of the matrix base material.

Item 24. The method according to any one of Items 21-23, wherein the matrix base material has a hydroxyl value of about 80 to about 350.

Item 25. The method according to any one of Items 21-24 further comprising a heat treatment step after the fusion coating.

Item 26. The method according to any one of Items 21-24 further comprising subjecting the core particles to heat treatment before the fusion coating.

Item 27. The method according to Item 25 or 26, wherein the heat treatment is conducted at a temperature from about 40° C. to about the melting point or the softening point of the matrix base material.

Item 28. The method according to any one of Items 21-27, wherein the polyglycerol fatty acid ester is a polyglycerol fatty acid half ester.

Item 29. The method according to any one of Items 21-27, wherein the polyglycerol fatty acid ester is a triglycerol behenic acid half ester.

Item 30. Medicament sustained release particles obtainable by the method according to any one of Items 21-29.

Item 31. Particles comprising a pharmacologically active substance and a matrix base material having a hydroxyl value of 60 or greater and containing a polyglycerol fatty acid ester, the pharmacologically active substance being uniformly dispersed throughout the matrix base material.

Item 32. Medicament sustained release particles each comprising the particle of Item 31 as nucleus particle and a coating layer comprising a fine powder and formed around the nucleus particle.

DETAILED DESCRIPTION OF THE INVENTION

Figure 1:
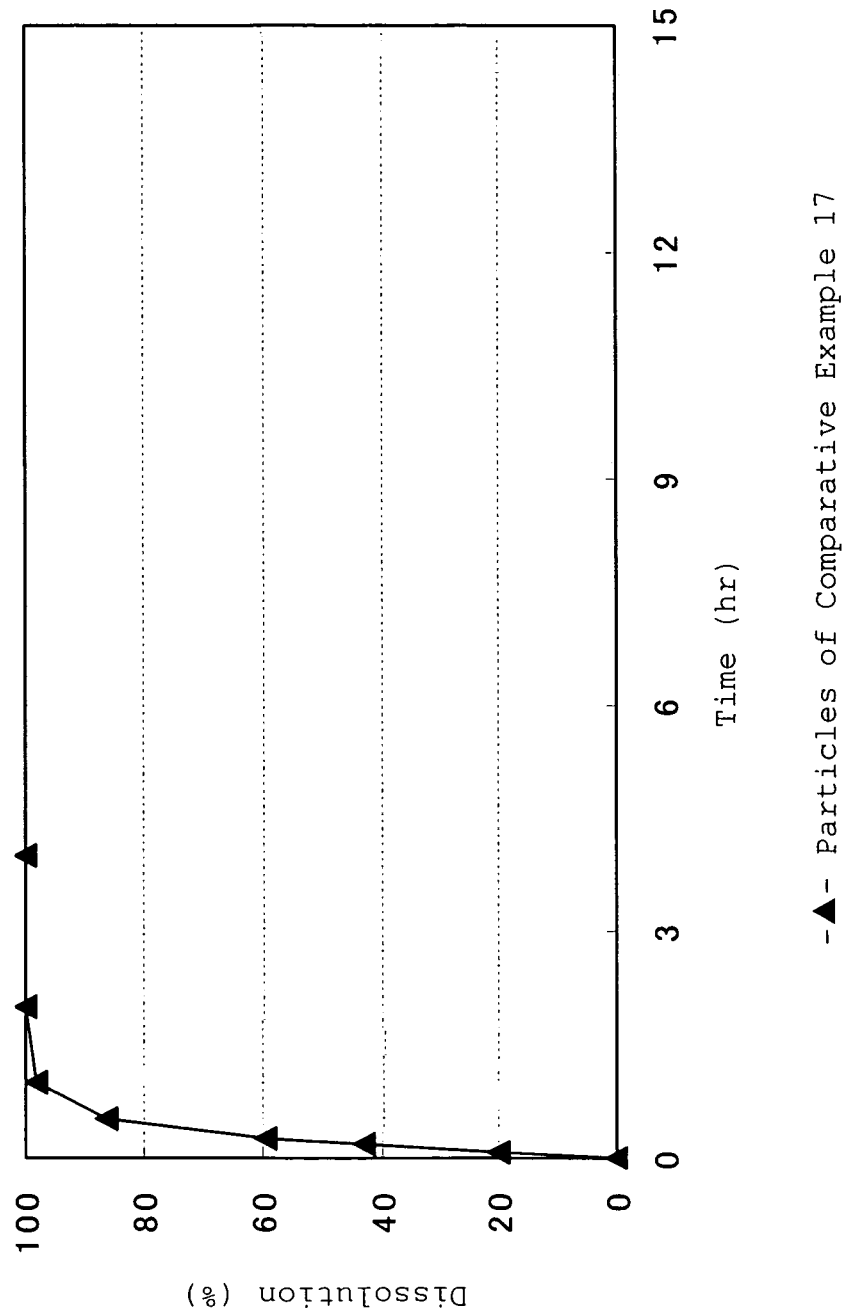
FIG. 1 is a graph showing the theophylline dissolution of the heat-treated fusion-coated particles of Comparative Example 17.

Theophylline sustained release particles and methods for preparing them (first embodiment), and medicament sustained release particles and methods for preparing them (second embodiment) will be described hereinbelow.

A. Theophylline Sustained Release Particles and Methods for Preparing them (First Embodiment)

The theophylline sustained release particles of the present invention are in the form of a matrix formulation containing theophylline. This sustained-release matrix formulation is in the form of particles and has a stably controlled theophylline releasability since theophylline is uniformly dispersed throughout the matrix. The theophylline sustained release particles of the present invention encompass core particles containing theophylline in a matrix, fusion-coated particles prepared by fusion coating such core particles with a fine powder such as talc powder or the like, and similar particles subjected to any necessary dilution process.

A-1. Core Particles

Theophylline

The core particles of the sustained-release particles of the present invention contain theophylline as a pharmacologically active substance. Theophylline can be either crystalline or amorphous in form. The core particles have a theophylline content of about 8 to about 50 wt. %, preferably about 15 to about 50 wt. % and more preferably about 20 to about 50 wt. %.

Matrix

The matrix of the core particles of the present invention contains a matrix base material containing a polyglycerol fatty acid ester as a main ingredient and further contains ethyl cellulose, and if desired other additives. The matrix base material may contain a glycerol fatty acid ester and the like in addition to the polyglycerol fatty acid ester.

Polyglycerol Fatty Acid Esters

The polyglycerol fatty acid ester used as the matrix base material is a fatty acid ester of polyglycerol.

Specific examples of polyglycerols are those that have a polymerization degree of 2-10, preferably 3-10. Usable are, for example, diglycerol, triglycerol, tetraglycerol, pentaglycerol, hexaglycerol, heptaglycerol, octaglycerol, nonaglycerol, decaglycerol, etc. Particularly usable are triglycerol, tetraglycerol, pentaglycerol, hexaglycerol, heptaglycerol, octaglycerol, nonaglycerol, decaglycerol, etc.

Usable fatty acids are, for example, saturated or unsaturated higher fatty acids having 12-22 carbon atoms and preferably 18-22 carbon atoms. Palmitic acid, stearic acid, oleic acid, linoleic acid, linolenic acid, myristic acid, lauric acid, ricinoleic acid, behenic acid and the like are usable as such fatty acids. In particular, stearic acid, oleic acid, behenic acid, ricinoleic acid and like saturated and unsaturated higher fatty acids having 18-22 carbon atoms are generally used.

A usable polyglycerol fatty acid ester is that in which $C_{12-22}$ fatty acid(s) are linked to the aforementioned polyglycerol with at least 1 hydroxyl group remaining therein. Specific examples of polyglycerol fatty acid esters are triglycerol behenic acid esters, triglycerol stearic acid esters, tetraglycerol behenic acid esters, tetraglycerol stearic acid esters, pentaglycerol behenic acid esters, pentaglycerol stearic acid esters, hexaglycerol behenic acid esters, hexaglycerol stearic acid esters, heptaglycerol behenic acid esters, heptaglycerol stearic acid esters, octaglycerol behenic acid esters, octaglycerol stearic acid esters, nonaglycerol behenic acid esters, nonaglycerol stearic acid esters, decaglycerol behenic acid esters, decaglycerol stearic acid esters and the like. Such esters can be used singly or as a mixture of 2 or more species. According to the number of hydroxyl groups in the polyglycerol, the polyglycerol fatty acid esters are categorized as fatty acid monoesters, diesters, triesters, tetraesters, pentaesters, hexaesters, half esters, etc.

Among these polyglycerol fatty acid esters, polyglycerol fatty acid half esters are preferable. In particular, triglycerol behenic acid half esters, tetraglycerol behenic acid half esters, pentaglycerol behenic acid half esters, hexaglycerol behenic acid half esters, heptaglycerol behenic acid half esters, octaglycerol behenic acid half esters, nonaglycerol behenic acid half esters, decaglycerol behenic acid half esters and like polyglycerol behenic acid half esters; and triglycerol stearic acid half esters, tetraglycerol stearic acid half esters, pentaglycerol stearic acid half esters, hexaglycerol stearic acid half esters, heptaglycerol stearic acid half esters, octaglycerol stearic acid half esters, nonaglycerol stearic acid half esters, decaglycerol stearic acid half esters and like polyglycerol stearic acid half esters are more preferably used. Triglycerol behenic acid half esters are most preferably used.

In the present specification and claims, polyglycerol fatty acid esters in which all the hydroxyl groups in a polyglycerol are esterified with fatty acids are referred to as polyglycerol fatty acid "full" esters, and polyglycerol fatty acid esters in which about half of the hydroxyl groups in the polyglycerol are esterified with fatty acids are referred to as polyglycerol fatty acid "half" esters. With respect to polyglycerol fatty acid esters other than the "polyglycerol fatty acid full esters", which hydroxyl groups in the polyglycerol are esterified are not limited; any given hydroxyl group may be esterified.

Specifically, a "polyglycerol fatty acid half ester" refers to a polyglycerol fatty acid ester or a mixture thereof in which the average number ($N_E$) of esterified hydroxyl groups in the polyglycerol is about the half of the number (N) of hydroxyl groups present in the non-esterified polyglycerol. Such polyglycerol fatty acid half esters have $0.3 \leq N_E/N \leq 0.7$, and preferably $0.35 \leq N_E/N \leq 0.65$.

For example, a triglycerol behenic acid half ester means an ester in which 2 or 3 behenic acids are ester-linked to a triglycerol having 5 hydroxyl groups, the triglycerol being 3 glycerol molecules dehydratively condensed, or a mixture thereof, i.e., triglycerol behenic acid (di or tri) ester.

The molecular weight of the polyglycerol fatty acid esters is usually 200-5000, preferably 300-2000 and more preferably 500-2000. Preferable are polyglycerol fatty acid esters that are solid at ordinary temperature (about 15° C.) and have a melting point of 15-90° C., and more preferably 45-80° C. Such polyglycerol fatty acid esters usable herein can be a mixture of 2 or more compounds. In such a case, even when a liquid polyglycerol fatty acid ester is partially contained, such a mixture is usable if it as a whole is solid at ordinary temperatures. The core particles have a polyglycerol fatty acid ester content of about 20 to about 90 wt. %, preferably about 25 to about 80 wt. % and more preferably about 30 to about 70 wt. %.

Glycerol Fatty Acid Esters

The glycerol fatty acid ester optionally used as a secondary ingredient of the matrix base material is a mono-, di- or tri $C_{12-22}$ fatty acid ester of a glycerol. Preferable glycerol fatty acid esters include glycerol behenic acid esters, glycerol stearic acid esters, glycerol lauric acid esters, glycerol palmitic acid esters, etc. If necessary, 2 or more glycerol fatty acid esters may be used in the matrix base material. Among such esters, glycerol behenic acid esters and glycerol stearic acid esters are preferable. Specific examples are glycerol stearic acid monoester, glycerol stearic acid diester, glycerol stearic acid triester, glycerol behenic acid monoester, glycerol behenic acid diester, glycerol behenic acid triester, etc. Among these, glycerol behenic acid esters are preferable, with glycerol behenic acid monoester, glycerol behenic acid diester and their mixtures being especially preferable.

The core particles have a glycerol fatty acid ester content of 0 to about 60 wt. %, preferably about 1 to about 50 wt. % and more preferably 2 to about 40 wt. %. The matrix base material preferable in the present invention contains both a glycerol fatty acid ester and a polyglycerol fatty acid ester.

Hydroxyl Value of Matrix Base Material

The matrix base material usable in the present invention can be prepared to have a hydroxyl value of about 60 or greater, preferably about 80 to about 350 and more preferably about 100 to about 300. Due to such a hydroxyl value, the core particles can be inhibited from electrostatically adhering to the inner walls of a granulator in the fusion coating process described hereinbelow, thereby allowing efficient fusion coating and the production of particles of a matrix formulation having a stably-controlled medicament releasability. The term "hydroxyl value" as used herein is defined in *Syokuhin Tenkabutsu Kouteisho* "Yushirui Shiken Hou" (*The Japanese Standards for Food Additives* "Testing Methods for Fats and Oils"), Hirokawa Shoten, 1999, B-195. In particular, the term "hydroxyl value" refers to, when the hydroxyl groups of a 1 g sample are acetylated, the amount (mg) of potassium hydroxide (KOH) necessary to neutralize acetic acid equivalent to acetyl group(s).

With respect to pharmaceutical preparations that sustainedly release pharmacologically active substances, it is generally considered preferable, to use polyglycerol fatty acid esters having a low hydrophilic-lipophilic balance (HLB) for the matrix to suppress the dissolution from the core particles. However, when the HLB of the matrix is low, the hydroxyl value is accordingly low, which results in a more pronounced tendency to electrostatically adhere to the inner walls of a granulator when fusion coating. To prevent this electrostatic adhesion, it is necessary to use core particles that barely accumulate an electrostatic charge. As a solution to this problem, a matrix base material having a hydroxyl value of preferably 60 or greater is used.

Glycerol fatty acid esters by themselves, especially monoglycerides (monoesters), barely adhere electrostatically to a granulator due to their high hydroxyl values. However, glycerol fatty acid esters and like lipids undergo crystalline transitions, thereby making it difficult to prepare stable pharmaceutical preparations. To inhibit crystalline transitions, it is preferable to have in the matrix base material 50 wt. % or more polyglycerol fatty acid ester. Therefore, the hydroxyl value of the polyglycerol fatty acid ester in the matrix base material is especially important. Hence, the hydroxyl value of the polyglycerol fatty acid ester should be controlled to be preferably about 60 or greater, more preferably about 80 to about 350 and particularly preferably about 100 to about 300.

Ethyl Cellulose

Ethyl cellulose is contained in the matrix of the core particles of the present invention. As described in the Disclosure of the Invention (a), when theophylline is added to a molten mixture prepared by heating a matrix base material containing a polyglycerol fatty acid ester, the viscosity of the molten mixture is excessively increased, making uniform blending difficult. This phenomenon is peculiar to theophylline when it is used as a medicament. However, if a small amount of ethyl cellulose is added to the theophylline-containing molten mixture, the viscosity of the mixture is promptly decreased, thereby drastically improving the workability with respect to stirring, mixing, fluid pumping, etc., and allowing the production of a uniformly blended molten mixture. By spray-cooling this molten mixture, homogenous particles of a matrix formulation having a stably controlled medicament releasability (dissolvability) can be obtained.

The viscosity of the ethyl cellulose, determined as a 5% ethyl cellulose solution in 80% toluene and 20% ethanol (at 25° C.), is usually preferably about 1 to about 100 cps, and particularly preferably about 2 to about 50 cps.

The core particles should usually be prepared to have an ethyl cellulose content of about 0.01 to about 5 wt. %, and preferably about 0.1 to about 3 wt. %. When the ethyl cellulose content is within this range, the desired decrease in the viscosity of the molten mixture can be observed.

Additives

Insofar as the action and effects of the present invention are not adversely affected, additives that are typically used in the field of sustained-release pharmaceutical preparations can be used in the matrix of the core particles of the present invention in addition to the compounds described above. Examples include propylene glycol fatty acid esters, sorbitan fatty acid esters, paraffin, microcrystalline wax, ceresin, hydrogenated oil, Japan wax, cacao butter, carnauba wax, beeswax, lecithin, cetanol, stearyl alcohol, myristic acid, palmitic acid, stearic acid, titanium stearate, calcium oleate, etc. These additives are contained in the core particles usually in an amount of 50 wt. % or less, and preferably 40 wt. % or less.

Preferable Form of Core particles

Examples of preferable forms of the core particles of the sustained theophylline release pharmaceutical preparation of the present invention are given below.

Although the matrix base material may be composed of just a polyglycerol fatty acid ester, it is preferable to also have a glycerol fatty acid ester. A polyglycerol behenic acid half ester is preferable as the polyglycerol fatty acid ester, and a triglycerol behenic acid half ester is particularly preferable. A glycerol behenic acid ester or glycerol stearic acid ester is preferable as the glycerol fatty acid ester, and a glycerol behenic acid monoester, a glycerol behenic acid diester and a mixture thereof are especially preferable.

Even when such a matrix base material is used, it is preferable to ensure 50 wt. % or greater of the entire weight of the matrix base material in the core particles is the polyglycerol fatty acid ester. It is sufficient that the weight ratio of polyglycerol fatty acid ester/glycerol fatty acid ester in the matrix base material is about 50/50 to about 95/5, and preferably about 50/50 to about 90/10.

The core particles have a theophylline content of about 15 to about 50 wt. %, preferably about 20 to about 50 wt. % and more preferably about 25 to about 45 wt. %. The core particles have a polyglycerol fatty acid ester content of about 25 to about 80 wt. % and preferably about 30 to about 70 wt. %. The core particles have a glycerol fatty acid ester content of about 1 to about 50 wt. %, preferably about 2 to about 40 wt. % and more preferably about 5 to about 35 wt. %. The core particles have an ethyl cellulose content of about 0.01 to about 5 wt. % and preferably about 0.1 to about 3 wt. %.

A-2. Method for Preparing Core Particles

The aforementioned core particles may be prepared as follows:

The matrix base material containing the polyglycerol fatty acid ester, theophylline and ethyl cellulose is heated to a liquefied mixture (or a molten mixture). This liquefied mixture is spray-cooled for granulation to give spherical core particles. The liquefied mixture includes a suspension mixture.

The temperature for fusing the matrix base material containing the polyglycerol fatty acid ester is high, ranging from the melting point (hereinafter sometimes referred to as "$T_m$") of the matrix base material upwards, and preferably from ($T_m$+10)° C. upwards, as long as such temperatures do not impair the stability of theophylline. When the matrix base material is a mixture, it may not exhibit a definite melting point. Therefore, the softening temperature (softening point, hereinafter sometimes referred to as "$T_s$") of the mixture can be substituted for the aforementioned $T_m$.

Hereinafter, the melting point ($T_m$) or softening point ($T_s$) of the matrix base material may sometimes be referred to as "T", i.e., T=$T_m$ or $T_s$.

To be able to uniformly dissolve (fuse) or disperse throughout the matrix base material, powdery ethyl cellulose with an average particle diameter of about 0.1 to about 200 μm, and preferably about 0.5 to about 150 μm, is usually used.

To be able to uniformly disperse throughout the matrix base material, powdery theophylline with an average particle diameter of about 0.1 to about 100 μm, and preferably about 0.5 to about 50 μm, is usually used.

Average particle diameters can be measured according to known methods such as laser light scattering and the like.

In the preparation of the molten mixture, the order of addition of theophylline and ethyl cellulose to the molten matrix base material is not restricted. After dissolving or dispersing theophylline in the molten matrix, ethyl cellulose may be dissolved (fused) or dispersed therein. Likewise, after dissolving (fusing) or dispersing ethyl cellulose in the molten matrix base material, theophylline may be dissolved or dispersed therein. Moreover, the dissolution or dispersion of theophylline and the dissolution (fusion) or dispersion of ethyl cellulose in the molten mixture can be carried out simultaneously.

When the theophylline sustained release particles of the present invention are to be in the form of powders, granules, microgranules, dry syrups, tablets, capsules and the like, a method preferably employed for the preparation of the molten mixture is heating and fusing the matrix base material, adding ethyl cellulose and theophylline into the molten matrix base material, and dissolving or dispersing the ethyl cellulose and theophylline therein to give a molten mixture. An example of particularly preferable method is adding premixed ethyl cellulose and theophylline into a molten matrix base material, and dissolving or dispersing to give a molten mixture.

The ingredients of the core particles are contained in the amounts as described in "A-1. Core particles" above. As described therein, in the method of the present invention, the viscosity of the molten mixture is significantly decreased by adding a small amount of ethyl cellulose, thereby allowing easy stirring and mixing. Thus, theophylline can be uniformly dispersed throughout the matrix base material, enabling the preparation of homogenous particles of a matrix formulation having a stably controlled medicament releasability (dissolvability).

The core particles can be prepared by spray-cooling the above-obtained molten mixture. Spray-cooling of the molten mixture can be performed according to conventional methods using, for example, a spray cooler equipped with a rotary disc, pressurized spray nozzle, two-fluid spray nozzle, etc. Cooling may usually be performed at room temperature. Appropriate control of the spraying conditions can give the desired diameter to the particles.

The core particles obtained according to such spray-cooling granulation are spherical, and their average particle diameter is usually 250 μm or less, preferably 200 μm or less, more preferably about 30 to about 200 μm, and particularly preferably about 50 to about 180 μm. The average particle diameter of the core particles can be measured according to known methods such as sieving.

Although the core particles obtained above can be used as they are in the fusion coating process that follows, they may be subjected to a heat treatment prior to the fusion coating. The heat treatment conditions are a temperature from about 40° C. to about T° C. at which the core particles do not fuse and adhere and a period of 2-48 hours (in particular, about 3 to about 24 hours). Due to this heat treatment, the crystalline transition of the matrix base material can be enhanced and completed, thereby enabling the theophylline release of the resulting product to be stabilized and thus giving sustained-release particles excellent storage stability.

The core particles of the present invention obtained as described above have a makeup in which theophylline and ethyl cellulose are uniformly dispersed throughout the matrix base material. Specifically, it is not a layered structure in which the theophylline and ethyl cellulose are localized at or adjacent to the surface of the matrix base material particles; rather the theophylline and ethyl cellulose are uniformly dispersed at the molecular level or as fine particles throughout the entire particles of the matrix base material, i.e., at the surface and within the particle structure.

Herein, the phrase "uniformly dispersed at the molecular level" means that theophylline, ethyl cellulose and the ester matrix form a homogeneous mixture of solids (solid dispersion). The phrase "uniformly dispersed as fine particles" means that theophylline and ethyl cellulose are evenly scattered as fine particles substantially throughout the entire matrix.

As described above, the core particles of the present invention, due to theophylline being uniformly dispersed throughout the matrix, can mask the bitterness of theophylline despite having an average particle diameter of about 30 to about 200 μm (preferably about 50 to about 180 μm) and so are very small, thereby enabling a stably controlled medicament releasability to be retained. Furthermore, the matrix base material is present at the surface of the core particles. This structure is suitable for fusion coating as described hereinbelow.

A-3. Fusion Coating

Fusion Coating

Fine powder is applied by fusion coating to the above-obtained core particles to further prepare the theophylline sustained release particles of the present invention. At least one member selected from, for example, talc, magnesium stearate, titanium oxide, ethyl cellulose, calcium stearate and cellulose acetate can be used as such a fine powder. Talc and ethyl cellulose are preferable. Talc is particularly preferable. Furthermore, if necessary, to eliminate any electrostatic charge that may build up on the particles during fusion coating, light anhydrous silicic acid and the like can be added. Unlike in spray coating, organic solvents are not used in fusion coating.

When the core particles obtained according to "A-2. Method for preparing core particles" are heated and fused, the molten matrix base material oozes toward the nucleus particle surface as a molten fluid. Due to the adhesiveness of the molten fluid in this instance, any fine powder present in the vicinity of the molten fluid adheres thereto. The fusion coating employed in the present invention is a technique to form, by taking advantage of the adhesiveness of the molten matrix base material, a coating (covering) layer containing fine powder on the surface of the core particles.

The average particle diameter of the fine powder varies according to the particle diameter of the core particles to be fusion-coated, but it is usually smaller than the diameter of the core particles. It is usually selected from the range of about 20 µm or smaller, preferably about 1 to about 15 µm and more preferably about 1 to about 10 µm.

The mixing ratio of core particles and fine powder may be determined according to the desired rate of theophylline release, diameter of the core particles and desired diameter of the end-product theophylline sustained release particles. The fine powder is usually used in an amount of about 5 to about 50 parts by weight, preferably about 10 to about 50 parts by weight and more preferably about 10 to about 45 parts by weight, per 100 parts by weight of core particles.

Fusion coating can be performed according to known methods. For example, the fine powder may be blended with the above-obtained core particles and heated while agitating. The heating temperature is about the melting point ($T_m$) or softening point ($T_s$) of the matrix base material, i.e., about T. The phrase "about T" refers to the range of (T−15)° C. to T° C., and preferably (T−10)° C. to T° C. For example, when the matrix base material is composed of a polyglycerol fatty acid ester and a glycerol fatty acid ester, it is in the range of about 40 to about 90° C., and preferably about 45 to about 80° C. The duration of fusion coating is, depending on the production scale, usually about 5 minutes to about 5 hours.

In the present invention, it is recommended to apply a fine powder to the core particles by fusion coating while agitating, i.e., using agitation method. Japanese Patent Publication No. 3124063 discloses a method in which powder is fused and adhered to polyglycerol fatty acid ester particles in a fluid bed. However, in fluid beds, to heat core particles to a temperature near their melting point, hot air having a temperature higher than the melting point is necessary, and because of the high temperature of the fluid-bed apparatus (side walls, meshed portion at the bottom, etc.) the core particles fuse, adhere to the apparatus, and aggregate, resulting in impaired yields. Moreover, it is practically impossible to tightly and completely affix powder to the core particles for the purpose of sustained medicament release. In contrast, when agitation method is employed, the container temperature (jacket temperature) of the mixer can be desirably controlled to a temperature substantially identical to the temperature of the core particles. Moreover, the entire apparatus can be rapidly cooled by introducing cold water into the jacket. Therefore, the core particles are barely overheated, completely preventing the core particles from aggregation due to fusion and adhesion to sidewalls.

The core particles after fusion coating are spherical and usually have an average particle diameter of 450 µm or less, preferably 400 µm or less, more preferably about 30 to about 400 µm and particularly preferably about 50 to about 350 µm.

The fusion-coated particles thus obtained are theophylline sustained release particles that have a fine-powder-containing coating layer around their core particles.

Thermal Aftertreatment

Although the fusion-coated particles obtained above can be brought as they are to the process that follows, it is preferable to subject the fusion-coated particles to a heat treatment beforehand. The heat treatment conditions are a temperature from about 40° C. to about T° C. at which the fusion-coated particles do not fuse and cluster and a period of 2-48 hours (preferably about 3 to about 24 hours). Due to this heat treatment, the crystalline transition of the matrix base material can be enhanced and completed, thereby enabling the theophylline release of the resulting product to be stabilized, and stable and extended theophylline release to be maintained even after long-term storage.

Specifically, after fusion coating, the aforementioned heat treatment is conducted in a shelf dryer, jacketed tank, jacketed mixer, jacketed vortex mixer or fluid bed. Heating methods are not limited. Heating temperatures vary according to the ingredients of the matrix base material. For example, the heat treatment may be conducted at about 40 to about 50° C. for a system containing a polyglycerol stearic acid ester and a glycerol stearic acid ester. For a system containing a polyglycerol behenic acid ester and a glycerol behenic acid ester, the heat treatment may be conducted at about 40 to about 60° C., with about 45 to about 55° C. being sometimes efficient.

With respect to a pharmaceutical preparation such as that disclosed in Japanese Patent Publication No. 2893191, i.e., a pharmaceutical preparation comprising core particles obtained by spray-cooling granulation of a molten mixture of a pharmacologically active substance and a mixture of a polyglycerol fatty acid ester and a lipid, the release rate of pharmacologically active substance is decreased over time once such a pharmaceutical preparation has been stored for a certain period of time at 40 or 50° C. This phenomenon is observable whenever the weight ratio of polyglycerol fatty acid ester/glycerol fatty acid ester is 50/50 to 90/10. In other words, when a polyglycerol fatty acid ester is used in combination with even a small amount of a glycerol fatty acid ester or other lipid, a crystalline transition progresses during high-temperature storage, thereby altering the rate of pharmacologically active substance release.

In contrast, the theophylline sustained release particles of the present invention, since the crystalline transition of the fusion-coated particles can be enhanced and completed by active heat treating, have a stably controlled theophylline releasability even after long-term storage (see Test Example 4, for example).

A-4. Dilution Process

By adding excipients and, as necessary, binders; mixing according to known methods; and granulating and, in some cases, compressing, the theophylline sustained release particles obtained according to "A-3. Fusion Coating" above can be formulated into powders, fine powders, granules, dry syrups, tablets and capsules.

As excipients, those that are usually used in this technical field can be widely used in the present invention, including mannitol, sorbitol, xylitol, erythritol, maltitol, glucose, saccharose, lactose and like saccharides; cornstarch, potatostarch and like starches; anhydrous calcium hydrogen phosphate, calcium phosphate and like inorganic salts; crystalline cellulose, sodium carboxymethyl starch; dextrin; macrogol (e.g., polyethylene glycol 6000, polyethylene glycol 4000, etc.); etc.

As binders, those that are usually used in this technical field can be widely used in the present invention, including methyl cellulose, hydroxypropyl cellulose, hydroxypropyl methyl cellulose, polyvinyl pyrrolidone, gelatin, gum arabic, polyvinyl alcohol, pullulan, macrogol (e.g., polyethylene glycol 6000, polyethylene glycol 4000,etc.), α-starch, partial α-starch, etc.

In the production of the pharmaceutical preparation having a sustained theophylline release of the present invention according to the method described above, disintegrators, surfactants, lubricants, plasticizers, sweeteners, colorants and various pharmaceutical carriers can be used in addition to the aforementioned excipients and binders.

As disintegrators, those that are usually used in this technical field can be widely used in the present invention, including low-substituted hydroxypropyl cellulose, sodium carboxymethyl starch, croscarmellose sodium, carboxymethyl cellulose, crystalline cellulose, crospovidone, etc.

As surfactants, those that are usually used in this technical field can be widely used in the present invention, including sodium lauryl sulfate, polysorbate 80, sucrose fatty acid ester, polyoxyethylene hydrogenated castor oil, etc.

As lubricants, those that are usually used in this technical field can be widely used in the present invention, including magnesium stearate, calcium stearate, polyoxyl stearate, talc, sucrose fatty acid ester, dimethyl polysiloxane, etc.

As plasticizers, those that are usually used in this technical field can be widely used in the present invention, including light anhydrous silicic acid and the like.

As sweeteners, those that are usually used in this technical field can be widely used in the present invention, including aspartame, fructose, xylitol, saccharin, sodium saccharin, saccharose, sucrose, sorbitol, lactose, glucose, mannitol, thaumatin, erythritol, etc.

As colorants, those that are usually used in this technical field can be widely used in the present invention, including coal-tar color and the like.

Flavorings such as menthol, orange flavor, etc., may be added to the sustained-release pharmaceutical preparation of the present invention obtained according to the method described above.

Excipients, binders, disintegrators, lubricants, plasticizers, sweeteners, colorants, flavorings and the like are used in amounts suitably selected in view of the type of medicaments used and desired resulting pharmaceutical preparation.

The theophylline sustained release particles after the dilution process usually have an average particle diameter of 500 μm or less, preferably 410 μm or less, more preferably about 30 to about 400 μm and particularly preferably about 50 to about 400 μm.

Moreover, the theophylline sustained release particles of the present invention have a stably controlled theophylline releasability (dissolvability). For example, when sustained-release particles that correspond to 100 mg theophylline are subjected to a theophylline dissolution test according to *The Japanese Pharmacopoeia*, 14$^{th}$ Edition, Dissolution Test (2$^{nd}$ Method, Paddle Method) at a stirring speed of 75 rpm using water or 0.5% aqueous polysorbate 80 solution as the test solution, the 2-hour theophylline dissolution rate is about 15 to about 55%, the 4-hour dissolution rate is about 25 to about 70% and 6-hour dissolution rate is about 50 to about 95%. Preferably, the 2-hour dissolution rate is about 20 to about 50%, the 4-hour dissolution rate is about 30 to about 65% and the 6-hour dissolution rate is about 55 to about 90%.

The theophylline sustained release particles of the present invention can be used as a pharmaceutical preparation in the form of, for example, powders, fine powders, granules, dry syrups, tablets, capsules, etc.

B. Medicament Sustained Release Particles and Methods for Preparing them (Second Embodiment)

The medicament sustained release particles of the present invention are in the form of a matrix formulation containing a pharmacologically active substance, and the matrix base material thereof has a hydroxyl value of 60 or greater. The use of such a matrix base material allows efficient fusion coating and the production of particulate sustained-release matrix formulation having a stably controlled medicament releasability. The medicament sustained release particles of the present invention encompass core particles containing a pharmacologically active substance in a matrix; fusion-coated particles prepared by fusion coating such core particles with a fine powder such as talc, a pharmacologically active substance and the like; and similar particles that subjected to any necessary dilution process.

B-1. Core particles

Matrix

The matrix of the core particles of the present invention contains a matrix base material having a hydroxyl value of 60 or greater and containing a polyglycerol fatty acid ester as a main ingredient and, if desired, further contains ethyl cellulose, other additives, etc. The matrix base material may contain a glycerol fatty acid ester and the like in addition to a polyglycerol fatty acid ester. In this case, the hydroxyl value of the matrix base material composed of the glycerol fatty acid ester and the polyglycerol fatty acid ester should still be 60 or greater.

When theophylline is used as a pharmacologically active substance, it is preferable that the core particles contain ethyl cellulose since the use of ethyl cellulose significantly enhances the mixing efficiency for a molten mixture of the matrix base material and theophylline in the preparation of core particles.

Polyglycerol Fatty Acid Esters

The polyglycerol fatty acid ester used as the matrix base material is a fatty acid ester of a polyglycerol. Polyglycerol fatty acid esters having a hydroxyl value of about 60 or greater are preferable.

Specific examples of polyglycerols are those that have a polymerization degree of 2-10 and preferably 3-10. Usable are, for example, diglycerol, triglycerol, tetraglycerol, pentaglycerol, hexaglycerol, heptaglycerol, octaglycerol, nonaglycerol, decaglycerol, etc. Particularly usable are triglycerol, tetraglycerol, pentaglycerol, hexaglycerol, heptaglycerol, octaglycerol, nonaglycerol, decaglycerol, etc.

Usable fatty acids are, for example, saturated or unsaturated higher fatty acids having 12-22 carbon atoms and preferably 18-22 carbon atoms. Palmitic acid, stearic acid, oleic acid, linoleic acid, linolenic acid, myristic acid, lauric acid, ricinoleic acid, behenic acid and the like are usable as such fatty acids. In particular, stearic acid, oleic acid, behenic acid, ricinoleic acid and like saturated and unsaturated higher fatty acids having 18-22 carbon atoms are generally used.

A usable polyglycerol fatty acid ester is that in which $C_{12-22}$ fatty acid(s) are linked to the aforementioned polyglycerol with at least 1 hydroxyl group remaining therein. Specific examples of polyglycerol fatty acid esters are triglycerol behenic acid esters, triglycerol stearic acid esters, tetraglycerol behenic acid esters, tetraglycerol stearic acid esters, pentaglycerol behenic acid esters, pentaglycerol stearic acid esters, hexaglycerol behenic acid esters, hexaglycerol stearic acid esters, heptaglycerol behenic acid esters, heptaglycerol stearic acid esters, octaglycerol behenic acid esters, octaglycerol stearic acid esters, nonaglycerol behenic acid esters, nonaglycerol stearic acid esters, decaglycerol behenic acid esters, decaglycerol stearic acid esters and the like. Such esters can be used singly or as a mixture of 2 or more species. According to the number of hydroxyl groups in the polyglycerol, the polyglycerol fatty acid esters are categorized as fatty acid monoesters, diesters, triesters, tetraesters, pentaesters, hexaesters, half esters, etc.

Among these polyglycerol fatty acid esters, polyglycerol fatty acid half esters are preferable. In particular, triglycerol behenic acid half esters, tetraglycerol behenic acid half esters, pentaglycerol behenic acid half esters, hexaglycerol behenic acid half esters, heptaglycerol behenic acid half esters, octaglycerol behenic acid half esters, nonaglycerol behenic acid half esters, decaglycerol behenic acid half esters and like polyglycerol behenic acid half esters; and triglycerol stearic acid half esters, tetraglycerol stearic acid half esters, pentaglycerol stearic acid half esters, hexaglycerol stearic acid half esters, heptaglycerol stearic acid half esters, octaglycerol stearic acid half esters, nonaglycerol stearic acid half esters, decaglycerol stearic acid half esters and like polyglycerol stearic acid half esters are more preferably used. Triglycerol behenic acid half esters are most preferably used.

Herein, polyglycerol fatty acid esters in which all the hydroxyl groups in a polyglycerol are esterified with fatty acids are referred to as polyglycerol fatty acid "full" esters, and polyglycerol fatty acid esters in which about half of the hydroxyl groups in the polyglycerol are esterified with fatty acids are referred to as polyglycerol fatty acid "half" esters. With respect to polyglycerol fatty acid esters other than the "polyglycerol fatty acid full esters", which hydroxyl groups in the polyglycerol are esterified are not limited; any given hydroxyl group may be esterified.

Specifically, a "polyglycerol fatty acid half ester" refers to a polyglycerol fatty acid ester or a mixture thereof in which the average number ($N_E$) of esterified hydroxyl groups in the polyglycerol is about the half of the number (N) of hydroxyl groups present in the non-esterified polyglycerol. Such polyglycerol fatty acid half esters have $0.3 \leq N_E/N \leq 0.7$, and preferably $0.35 \leq N_E/N \leq 0.65$.

For example, a triglycerol behenic acid half ester means an ester in which 2 or 3 behenic acids are ester-linked to a triglycerol having 5 hydroxyl groups, the triglycerol being 3 glycerol molecules dehydratively condensed, or a mixture thereof, i.e., triglycerol behenic acid (di or tri) ester.

The molecular weight of the polyglycerol fatty acid esters is usually 200-5000, preferably 300-2000 and more preferably 500-2000. Preferable are polyglycerol fatty acid esters that are solid at ordinary temperature (about 15° C.) and have a melting point of 15-90° C., and more preferably 45-80° C. Such polyglycerol fatty acid esters usable herein can be a mixture of 2 or more compounds. In such a case, even when a liquid polyglycerol fatty acid ester is partially contained, such a mixture is usable if it as a whole is solid at ordinary temperatures. The core particles has a polyglycerol fatty acid ester content of about 20 to about 99.999 wt. %, preferably about 25 to about 95 wt. % and more preferably about 30 to about 90 wt. %.

Glycerol Fatty Acid Esters

The glycerol fatty acid ester optionally used as a secondary ingredient of the matrix base material is a $C_{12-22}$ fatty acid ester of a glycerol. Preferable glycerol fatty acid esters include glycerol behenic acid esters, glycerol stearic acid esters, glycerol lauric acid esters, glycerol palmitic acid esters, etc. If necessary, 2 or more glycerol fatty acid esters may be used in the matrix base material. Among such esters, glycerol behenic acid esters and/or glycerol stearic acid esters are preferable. Specific examples are glycerol stearic acid monoester, glycerol stearic acid diester, glycerol stearic acid triester, glycerol behenic acid monoester, glycerol behenic acid diester, glycerol behenic acid triester, etc. Among these, glycerol behenic acid esters are preferable, with glycerol behenic acid monoester, glycerol behenic acid diester and their mixtures being especially preferable.

The core particles have a glycerol fatty acid ester content of 0 to about 60 wt. %, preferably about 1 to about 50 wt. % and more preferably 2 to about 40 wt. %. The matrix base material preferable in the present invention contains both a glycerol fatty acid ester and a polyglycerol fatty acid ester.

Hydroxyl Value of Matrix Base Material

The matrix base material usable in the present invention has a hydroxyl value of about 60 or greater, preferably about 80 to about 350 and more preferably about 100 to about 300. Due to such a hydroxyl value, the core particles can be inhibited from electrostatically adhering to the inner walls of a granulator in the fusion coating process described hereinbelow, thereby allowing efficient fusion coating and the production of particles of a matrix formulation having a stably controlled medicament releasability. The term "hydroxyl value" as used herein is defined in *Syokuhin Tenkabutsu Kouteisho* "Yushirui Shiken Hou" (*The Japanese Standards for Food Additives* "Testing Methods for Fats and Oils"), Hirokawa Shoten, 1999, B-195. In particular, the term "hydroxyl value" refers to, when the hydroxyl groups of a 1 g sample are acetylated, the amount (mg) of potassium hydroxide (KOH) necessary to neutralize acetic acid equivalent to acetyl group (s).

With respect to pharmaceutical preparations that sustainedly release pharmacologically active substances, it is generally considered preferable, to use polyglycerol fatty acid esters having a low hydrophilic-lipophilic balance (HLB) for the matrix to suppress the dissolution from the core particles. However, when the HLB of the matrix is low, the hydroxyl value is accordingly low, which results in a more pronounced tendency to electrostatically adhere to the inner walls of a granulator when fusion coating. To prevent this electrostatic adhesion, it is necessary to use core particles that barely accumulate an electrostatic charge. As a solution to this problem, a matrix base material having a hydroxyl value of preferably 60 or greater is used.

Glycerol fatty acid esters by themselves, especially monoglycerides (monoesters), barely adhere electrostatically to a granulator due to their high hydroxyl values. However, glycerol fatty acid esters and like lipids undergo crystalline transitions, thereby making it difficult to prepare stable pharmaceutical preparations. To inhibit crystalline transitions, it is preferable to have in the matrix base material 50 wt. % or more polyglycerol fatty acid ester. Therefore, the hydroxyl value of the polyglycerol fatty acid ester in the matrix base material is especially important. Hence, the hydroxyl value of the polyglycerol fatty acid ester should be controlled to be preferably about 60 or greater, more preferably about 80 to about 350 and particularly preferably about 100 to about 300.

Pharmacologically Active Substances

The pharmacologically active substances that can be used in the medicament sustained release particles of the present invention are not limited, and known substances can be widely used. Examples of such pharmacologically active substances include those typically used in a variety of pharmaceutical preparations such as antibiotics, antifungal agents, antilipemics, circulatory drugs, antiplatelets (platelet aggregation inhibitors), antitumor agents, antipyretics, analgesics, antiphlogistics, antitussive/expectorating agents, tranquillizers, muscle relaxants, antiepileptic agents, antiulcer agents, antidepressants, antiallergy agents, cardiac stimulants, antiarrhythmics, vasodilators, hypotensive diuretics, diabetic medicines, anticoagulants, hemostatic agents, antituberculosis drugs, hormone drugs, narcotic antagonists, bone-resorption inhibitors, vascularization inhibitors, antipodagrics, etc.

Specific examples include theophylline, cilostazol, grepafloxacin, carteolol, procaterol, rebamipide, aripiprazole, etc. The group of pharmacologically active substances described above can be used singly or in combination.

The core particles have a pharmacologically active substance content of about 0.001 to about 60 wt. %, preferably about 0.01 to about 55 wt. % and more preferably about 0.1 to about 50 wt. %.

Ethyl Cellulose

Ethyl cellulose may be contained in the matrix of the core particles of the present invention. In particular, when theophylline is used as a pharmacologically active substance, ethyl cellulose should be used. As described in the Disclosure of the Invention (a), when theophylline is added to a molten mixture prepared by heating a matrix base material containing a polyglycerol fatty acid ester, the viscosity of the molten mixture is excessively increased, making uniform blending difficult. This phenomenon is peculiar to theophylline when it is used as a medicament. However, if a small amount of ethyl cellulose is added to the theophylline-containing molten mixture, the viscosity of the mixture is promptly decreased, thereby drastically improving the workability with respect to stirring, mixing, pumping, etc., and allowing the production of a uniformly blended molten mixture. By spray-cooling this molten mixture, homogenous particles of a matrix formulation having a stably controlled medicament releasability (dissolvability) can be obtained.

The viscosity of the ethyl cellulose, determined as a 5% ethyl cellulose solution in 80% toluene and 20% ethanol (at 25° C.), is usually preferably about 1 to about 100 cps, and particularly preferably about 2 to about 50 cps.

When theophylline is used as a pharmacologically active substance, the core particles are prepared to have an ethyl cellulose content of about 0.01 to about 5 wt. %, preferably about 0.1 to about 3 wt. %. When the ethyl cellulose content is within this range, a preferable decrease in the viscosity of the molten mixture can be observed.

Additives

Insofar as the action and effects of the present invention are not adversely affected, additives that are typically used in the field of sustained-release pharmaceutical preparations can be used in the matrix of the core particles of the present invention in addition to the compounds described above. Examples include propylene glycol fatty acid esters, sorbitan fatty acid esters, paraffin, microcrystalline wax, ceresin, hydrogenated oil, Japan wax, cacao butter, carnauba wax, beeswax, lecithin, cetanol, stearyl alcohol, myristic acid, palmitic acid, stearic acid, titanium stearate, calcium oleate, etc. These additives are contained in the core particles usually in an amount of 50 wt. % or less, and preferably 40 wt. % or less.

Preferable Form of Core Particles

Examples of preferable forms of the core particles of the sustained theophylline release pharmaceutical preparation of the present invention are given below.

Examples of pharmacologically active substances are theophylline, cilostazol, grepafloxacin, carteolol, procaterol, rebamipide, aripiprazole, etc., with theophylline being particularly preferable. Although the matrix base material may be composed of just a polyglycerol fatty acid ester, it is preferable to also have a glycerol fatty acid ester. A polyglycerol behenic acid half ester is preferable as the polyglycerol fatty acid ester, and a triglycerol behenic acid half ester is particularly preferable. A glycerol behenic acid ester or glycerol stearic acid ester is preferable as the glycerol fatty acid ester, and a glycerol behenic acid monoester, a glycerol behenic acid diester and a mixture thereof are especially preferable.

Even when such a matrix base material is used, it is preferable to ensure 50 wt. % or greater of the entire weight of the matrix base material in the core particles is the polyglycerol fatty acid ester. It is sufficient that the weight ratio of polyglycerol fatty acid ester/glycerol fatty acid ester in the matrix base material is about 50/50 to about 99/1, and preferably about 50/50 to about 90/10.

The core particles have a pharmacologically active substance content (preferably a theophylline content) of about 15 to about 50 wt. %, preferably about 20 to about 50 wt. % and more preferably about 25 to about 45 wt. %. The core particles have a polyglycerol fatty acid ester content of about 25 to about 80 wt. % and preferably about 30 to about 70 wt. %. The core particles have a glycerol fatty acid ester content of about 1 to about 50 wt. %, preferably about 2 to about 40 wt. % and more preferably about 5 to about 35 wt. %. In particularly, when theophylline is used, the core particles should have an ethyl cellulose content of about 0.01 to about 5 wt. % and preferably about 0.1 to about 3 wt. %.

When the core particles contain relatively low proportions of active ingredients, the content of each ingredient can be arranged to be in the following ranges. For example, when the core particles contain active ingredients in about 0.001 to about 10 wt. %, the core particles may contain the matrix base material in about 90 to about 99.999 wt. %. When the core particles contain active ingredients in about 0.01 to about 10 wt. %, the core particles may contain the matrix base material in about 90 to about 99.99 wt. %. The weight ratio of polyglycerol fatty acid ester/glycerol fatty acid ester in the matrix base material may be 50/50 to 95/1, preferably 50/50 to 90/10.

B-2. Method for Preparing Core Particles

The aforementioned core particles may be prepared as follows:

The matrix base material containing the polyglycerol fatty acid ester and pharmacologically active substance are heated to a liquefied mixture (or a molten mixture). This liquefied mixture is spray-cooled for granulation to give spherical core particles. The liquefied mixture includes a suspension mixture.

The temperature for fusing the matrix base material containing the polyglycerol fatty acid ester is high, ranging from the melting point (hereinafter sometimes referred to as "$T_m$") of the matrix base material upwards, and preferably from $(T_m+10)°$ C. upwards, as long as such temperatures do not impair the stability of pharmacologically active substance. When the matrix base material is a mixture, it may not exhibit a definite melting point. Therefore, the softening temperature (softening point, hereinafter sometimes referred to as "$T_s$") of the mixture can be substituted for the aforementioned $T_m$.

Hereinafter, the melting point ($T_m$) or softening point ($T_s$) of the matrix base material may sometimes be referred to as "T", i.e., $T = T_m$ or $T_s$.

To be able to uniformly dissolve (fuse) or disperse throughout the matrix base material, a powdery pharmacologically active substance that has an average particle diameter of about 0.1 to about 100 μm, preferably about 0.5 to about 50 μm, is usually used.

Average particle diameters can be measured according to known methods such as laser light scattering and the like.

Methods for heating the matrix base material and pharmacologically active substance to give a molten mixture are not limited. An exemplary method employed for the preparation of the molten mixture is heating and fusing the matrix base material; adding a pharmacologically active substance and, as necessary, other ingredients into the molten matrix base material; and dissolving or dispersing therein to give a molten mixture.

The ingredients of the core particles are contained in the amounts as described in "B-1. Core particles" above. When theophylline is used as a pharmacologically active substance, it is preferable to also use ethyl cellulose. The core particles are usually prepared to have an ethyl cellulose content of about 0.01 to about 5 wt. %, preferably about 0.1 to about 3 wt. %. By the addition of a small amount of ethyl cellulose, the viscosity of the molten mixture is significantly decreased, thereby allowing easy stirring and mixing. Thus, theophylline can be uniformly dispersed throughout the matrix base material, enabling the preparation of homogenous particles of a matrix formulation having a stably controlled medicament releasability (dissolvability).

The core particles can be prepared by spray-cooling the above-obtained molten mixture. Spray-cooling of the molten mixture can be performed according to conventional methods using, for example, a spray cooler equipped with a rotary disc, pressurized spray nozzle, two-fluid spray nozzle, etc. Cooling may usually be performed at room temperature. Appropriate control of the spraying conditions can give the desired diameter to the particles.

The core particles obtained according to such spray-cooling granulation are spherical, and their average particle diameter is usually 250 μm or less, preferably 200 μm or less, more preferably about 30 to about 200 μm, and particularly preferably about 50 to about 180 μm. The average particle diameter of the core particles can be measured according to known methods such as sieving.

Although the core particles obtained above can be used as they are in the fusion coating process that follows, they may be subjected to a heat treatment prior to the fusion coating. The heat treatment conditions are a temperature from about 40° C. to about T° C. at which the core particles do not fuse and adhere and a period of 2-48 hours (in particular, about 3 to about 24 hours). Due to this heat treatment, the crystalline transition of the matrix base material can be enhanced and completed, thereby enabling the release of pharmacologically active substance of the resulting product to be stabilized and thus giving sustained-release particles excellent storage stability.

The core particles of the present invention obtained as described above have a makeup in which a pharmacologically active substance is uniformly dispersed throughout the matrix. Specifically, it is not a layered structure in which the pharmacologically active substance is localized at or adjacent to the surface of the matrix base material particles; rather the pharmacologically active substance is uniformly dispersed at the molecular level or as fine particles throughout the entire particles of the matrix base material, i.e., at the surface and within the particle structure.

Herein, the phrase "uniformly dispersed at the molecular level" means that theophylline, ethyl cellulose and the ester matrix form a homogeneous mixture of solids (solid dispersion). The phrase "uniformly dispersed as fine particles" means that theophylline and ethyl cellulose are evenly scattered as fine particles substantially throughout the entire matrix.

As described above, the core particles of the present invention, due to the pharmacologically active substance being uniformly dispersed throughout the matrix, can mask its bitterness despite having an average particle diameter of about 30 to about 200 μm (preferably about 50 to about 180 μm) and so are very small, thereby enabling a stably controlled medicament releasability to be retained. Furthermore, the matrix base material is present at the surface of the core particles. This structure is suitable for fusion coating as described hereinbelow.

B-3. Fusion Coating
Fusion Coating

Fine powder is applied by fusion coating to the above-obtained core particles to further prepare the medicament sustained release particles of the present invention. As such a fine powder, (a) at least one member selected from, for example, talc, magnesium stearate, titanium oxide, ethyl cellulose, calcium stearate and cellulose acetate, or (b) pharmacologically active substances can be used. Examples of (b) pharmacologically active substances are those described in "B-1. Core particles" above. Furthermore, if necessary, to eliminate any electrostatic charge that may build up on the particles during fusion coating, light anhydrous silicic acid and the like may be added. Unlike in spray coating, organic solvents are not used in fusion coating.

When the core particles obtained according to "B-2. Method for preparing core particles" are heated and fused, the molten matrix base material oozes toward the nucleus particle surface as a molten fluid. Due to the adhesiveness of the molten fluid in this instance, any fine power present in the vicinity of the molten fluid adheres thereto. The fusion coating employed in the present invention is a technique to form, by taking advantage of the adhesiveness of the molten matrix base material, a coating (covering) layer containing fine powder on the surface of the core particles.

The average particle diameter of the fine powder varies according to the particle diameter of the core particles to be fusion-coated, but it is usually smaller than the diameter of the core particles. It is usually selected from the range of about 20 μm or smaller, preferably about 1 to about 15 μm and more preferably about 1 to about 10 μm.

The mixing ratio of core particles and fine powder may be determined according to the desired rate of meidcament release, diameter of the core particles and desired particle diameter of the end-product pharmaceutical preparation with a sustained medicament release. The fine powder is usually used in an amount of about 5 to about 50 parts by weight, preferably about 10 to about 50 parts by weight and more preferably about 10 to about 45 parts by weight, per 100 parts by weight of core particles.

Fusion coating can be performed according to known methods. For example, the fine powder may be blended with the above-obtained core particles and heated while agitating. The heating temperature is about the melting point ($T_m$) or softening point ($T_s$) of the matrix base material, i.e., about T. The phrase "about T" refers to the range of (T-15)° C. to T° C., and preferably (T-10)° C. to T° C. For example, when the matrix base material is composed of a polyglycerol fatty acid ester and a glycerol fatty acid ester, it is in the range of about 40 to about 90° C., and preferably about 45 to about 80° C. The duration of fusion coating is, depending on the production scale, usually about 5 minutes to about 5 hours.

In the present invention, the fusion coating of the core particles with fine powder may be performed by taking advantage of either agitating (agitation method) or a fluid bed (fluid-bed method). When coating is performed while agitating, conventional mixer/granulators may be used. When coating is performed in a fluid bed, conventional fluid-bed granulators may be used. The fusion coating is particularly preferably performed with agitation.

In fluid beds, to heat core particles to a temperature near their melting point, hot air having a temperature higher than the melting point is necessary, and because of the high temperature of the fluid-bed apparatus (side walls, meshed portion at the bottom, etc.) the core particles fuse, adhere to the apparatus, and cluster, resulting in impaired yields. Moreover, it is sometimes practically impossible to tightly and completely affix powder to the core particles for the purpose of sustained medicament release. In contrast, when agitation method is employed, the container temperature (jacket temperature) of the mixer can be desirably controlled to a temperature substantially identical to the temperature of the core particles. Moreover, the entire apparatus can be rapidly cooled by introducing cold water into the jacket. Therefore, the core particles are barely overheated, completely preventing the core particles from aggregating due to fusion and adhesion to sidewalls.

The core particles after fusion coating are spherical and usually have an average particle diameter of 450 µm or less, preferably 400 µm or less, more preferably about 30 to about 400 µm and particularly preferably about 50 to about 350 µm.

The fusion-coated particles thus obtained are theophylline sustained release particles that have a fine-powder-containing coating layer around their core particles.

Thermal Aftertreatment

Although the fusion-coated particles obtained above can be brought as they are to the process that follows, it is preferable to subject the fusion-coated particles to a heat treatment beforehand. The heat treatment conditions are a temperature from about 40° C. to about the melting point (softening point) of the matrix base material at which the fusion-coated particles do not fuse and aggregate and a period of 2-48 hours (preferably about 3 to about 24 hours). Due to this heat treatment, the crystalline transition of the matrix base material can be enhanced and completed, thereby enabling the release the pharmacologically active substance of the resulting product to be stabilized, and stable and extended the pharmacologically active substance release to be maintained even after long-term storage.

Specifically, after fusion coating, the aforementioned heat treatment is conducted in a jacketed mixer, vortex mixer or fluid bed. Heating methods are not limited. Heating temperatures vary according to the ingredients of the matrix base material. For example, the heat treatment may be conducted at about 40 to about 50° C. for a system containing a polyglycerol stearic acid ester and a glycerol stearic acid ester. For a system containing a polyglycerol behenic acid ester and a glycerol behenic acid ester, the heat treatment may be conducted at about 40 to about 60° C., with about 45 to about 55° C. being sometimes efficient.

With respect to a pharmaceutical preparation such as that disclosed in Japanese Patent Publication No. 2893191, i.e., a pharmaceutical preparation comprising core particles obtained by spray-cooling granulation of a molten mixture of a pharmacologically active substance and a mixture of a polyglycerol fatty acid ester and a lipid, the release rate of pharmacologically active substance is decreased over time once such a pharmaceutical preparation has been stored for a certain period of time at 40 or 50° C. This phenomenon is observable whenever the weight ratio of polyglycerol fatty acid ester/glycerol fatty acid ester is 50/50 to 90/10. In other words, when a polyglycerol fatty acid ester is used in combination with even a small amount of a glycerol fatty acid ester or other lipid, a crystalline transition progresses during high-temperature storage, thereby altering the rate of pharmacologically active substance release.

In contrast, the theophylline sustained release particles of the present invention, since the crystalline transition of the fusion-coated particles can be enhanced and completed by active heat treating, have a stably controlled theophylline releasability even after long-term storage (see Test Example 4, for example).

B-4. Dilution Process

The sustained medicament release pharmaceutical preparation obtained by "B-3. Fusion Coating" above may be subjected to a dilution process. The dilution process is as described in "A-4. Dilution Process" above.

The medicament sustained release particles of the present invention after a dilution process usually have an average particle diameter of 500 µm or less, preferably 410 µm or less, more preferably about 30 to about 350 µm and particularly preferably about 50 to about 350 µm.

Moreover, the medicament sustained release particles of the present invention have the property of retaining an extended release (dissolvability) of a pharmacologically active substance. For example, when sustained-release particles that correspond to 100 mg of pharmacologically active substance are subjected to a pharmacologically active substance dissolution test according to The Japanese Pharmacopoeia, $14^{th}$ Edition, Dissolution Test ($2^{nd}$ Method, Paddle Method) at a stirring speed of 75 rpm using water or 0.5% aqueous polysorbate 80 solution-as the test solution, the 2-hour dissolution rate is about 15-55%, the 4-hour dissolution rate is about 25-70% and 6-hour dissolution rate is about 50-95%. Preferably, the 2-hour dissolution rate is about 20-50%, the 4-hour dissolution rate is about 30-65% and the 6-hour dissolution rate is about 55-90%.

The medicament sustained release particles of the present invention can be used as a pharmaceutical preparation in the form of, for example, powders, fine powders, granules, dry syrups, tablets, capsules, etc.

BEST MODE FOR CARRYING OUT THE INVENTION

Examples are given below to illustrate the present invention in more detail, but the scope of the invention is not limited to these examples. The symbols "%" in the tables mean "wt. %" unless specified otherwise.

<Ingredients Used in the Examples>

Theophylline

Poem B-100: Riken Vitamin Co., Ltd., glycerol behenic acid monoester

Poem B-200: Riken Vitamin Co., Ltd., glycerol behenic acid ester (including mono- and diesters)

Glycerol monostearic acid ester P-100: Riken Vitamin Co., Ltd., glycerol monostearic acid ester J-46B: Riken Vitamin Co., Ltd., tetraglycerol hexabehenic acid ester TR-HB: Riken Vitamin Co., Ltd., triglycerol behenic acid half ester TR-FB: Riken Vitamin Co., Ltd., triglycerol behenic acid full ester TR-2B: Riken Vitamin Co., Ltd., triglycerol monobehenic acid ester DI-FB: Riken Vitamin Co., Ltd., diglycerol behenic acid full ester DDB-750: Sakamoto Yakuhin Kogyo Co., Ltd., decaglycerol heptabehenic acid ester HB-750: Sakamoto Yakuhin Kogyo Co., Ltd., decaglycerol dodecabehenic acid ester Ethyl cellulose (EC) (7 cps): Dow Chemical Company, ethyl cellulose 7 cps
Ethyl cellulose (EC) (10 cps)-FP: Dow Chemical Company, ethyl cellulose 10 cps-FP
Talc
Light anhydrous silicic acid
Sucrose (ground)
D-mannitol
Polysorbate 80
Sodium lauryl sulfate

TEST EXAMPLE 1

Reduction in the Viscosity of Molten Mixture by the Addition of EC

A polyglycerol fatty acid ester and, as necessary, a glycerol fatty acid ester were heated and fused. A medicament (theophylline, rebamipide or cilostazol) was dispersed therein using a homogenizer. The viscosity of the molten mixtures was measured by a model C viscometer. Likewise, molten mixtures were prepared in the same manner except that EC (7 cps) or cellulose acetate was further added. The viscosity of these molten mixtures was also measured. Tables 1-6 below show the results of Examples 1-12, Comparative Examples 1-9 and Reference Examples 1-7.

TABLE 1

|  | Comp. Ex. 1 | Ex. 1 | Comp. Ex. 2 | Ex. 2 | Ex. 3 | Ex. 4 |
| --- | --- | --- | --- | --- | --- | --- |
| Theophylline | 40.0% | 39.7% | 40% | 40% | 39.2% | 39.5% |
| EC (7 cps) | 0.0% | 0.7% | 0% | 1% | 2.0% | 3.1% |
| B-100 | 0.0% | 0.0% | 30% | 30% | 29.4% | 28.7% |
| TR-HB | 60.0% | 59.6% | 30% | 29% | 29.4% | 28.7% |
| Total | 100.0% | 100.0% | 100% | 100% | 100.0% | 100.0% |
| Viscosity (mPa·s) | 4000 | 2000 | 1200 | 320-360 | 400 | 600-680 |

TABLE 2

|  | Comp. Ex. 3 | Ex. 5 | Comp. Ex. 4 | Ex. 6 | Ex. 7 | Ex. 8 |
| --- | --- | --- | --- | --- | --- | --- |
| Theophylline | 40% | 40% | 40.0% | 40.0% | 40.0% | 40.0% |
| EC (7 cps) | 0% | 1% | 0.0% | 1.0% | 3.0% | 5.0% |
| B-100 | 0% | 0% | 18.3% | 18.0% | 17.4% | 16.8% |
| HB-750 | 60% | 59% | 41.7% | 41.0% | 39.6% | 38.2% |
| Total | 100% | 100% | 100.0% | 100.0% | 100.0% | 100.0% |
| Viscosity (mPa·s) | 3800 | 1600 | 900 | 420 | 440 | 600 |

TABLE 3

|  | Comp. Ex. 5 | Ex. 9 | Ex. 10 | Ex. 11 | Ex. 12 |
| --- | --- | --- | --- | --- | --- |
| Theophylline | 40.0% | 39.9% | 39.7% | 40.1% | 40.0% |
| EC (7 cps) | 0.0% | 0.3% | 0.7% | 1.3% | 3.0% |
| DDB-750 | 60.0% | 59.8% | 59.6% | 58.6% | 57.0% |
| Total | 100.0% | 100.0% | 100.0% | 100.0% | 100.0% |
| Viscosity (mPa·s) | 1160 | 480 | 460 | 540 | 880 |

TABLE 4

|  | Comp. Ex 6 | Comp. Ex. 7 | Comp. Ex. 8 | Comp. Ex. 9 |
| --- | --- | --- | --- | --- |
| Theophylline | 40.0% | 39.9% | 39.7% | 40.1% |
| Cellulose acetate (10 NF*) | 0.0% | 0.3% | 0.7% | 1.3% |
| TR-HB | 60.0% | 59.8% | 59.6% | 58.6% |
| Total | 100.0% | 100.0% | 100.0% | 100.0% |
| Viscosity (mPa·s) | 1520 | 1560 | 1640 | 1960 |

*a product in conformity with USP/NF of U.S.A.

TABLE 5

|  | Ref. Ex. 1 | Ref. Ex. 2 | Ref. Ex. 3 |
| --- | --- | --- | --- |
| Rebamipide | 35.7% | 35.6% | 35.5% |
| EC (7 cps) | 0.0% | 0.4% | 0.7% |
| TR-HB | 64.3% | 64% | 63.8% |
| Total | 100.0% | 100.0% | 100.0% |
| Viscosity (mPa·s) | 1320 | 1400 | 1520 |

TABLE 6

|  | Ref. Ex. 4 | Ref. Ex. 5 | Ref. Ex. 6 | Ref. Ex. 7 |
| --- | --- | --- | --- | --- |
| Cilostazol | 10.0% | 9.9% | 9.9% | 9.7% |
| EC (7 cps) | 0.0% | 0.7% | 1.4% | 2.8% |
| B-100 | 28.6% | 28.4% | 28.2% | 27.8% |
| J-46B | 61.4% | 61.0% | 60.5% | 59.7% |
| Total | 100.0% | 100.0% | 100.0% | 100.0% |
| Viscosity (mPa·s) | 920 | 860 | 780 | 820 |

When the results of Comparative Example 1 and Example 1 shown in Table 1 and the results of Comparative Example 3 and Example 5 shown in Table 2 are considered, the effect of ethyl cellulose in decreasing viscosity is evident. In other words, when the matrix base material is composed only of a polyglycerol fatty acid ester (TR-HB or HB-750), the molten mixtures exhibited high viscosity (4000 for Comparative Example 1 and 3800 for Comparative Example 3). Hence, it was difficult to uniformly disperse the medicament in the respective matrices. In contrast, when a small amount of EC was added, the viscosity of the molten mixtures was greatly decreased (2000 for Example 1 and 1600 for Example 5).

In view of the results of Comparative Example 2 and Examples 2-4 shown in Table 1 and the results of Comparative Example 4 and Examples 6-8 shown in Table 2, when the matrix base material is composed of a polyglycerol fatty acid ester (TR-HB or HB-750) and a glycerol behenic acid ester (B-100), the molten mixtures exhibited high viscosity. However, when a small amount of EC was added, the viscosity of the molten mixtures was greatly decreased.

Considering the results shown in Tables 1-3, it is preferable to add EC in a specific proportion relative to the molten mixture. When the amount of EC is excessive, viscosity is increased. In other words, when the proportion of theophylline, polyglycerol fatty acid ester, and, as necessary, glycerol fatty acid ester contained in the molten mixture stays constant, a significant decrease in the viscosity of the molten mixture can be observed with the addition of a specific proportion of EC.

As shown in Table 4, when cellulose acetate was used in place of EC, a decrease in the viscosity of the molten mixtures was not observed.

As shown in Tables 5 and 6, when other pharmacologically active substances (i.e., rebamipide and cilostazol) were used in place of theophylline, a decrease in the viscosity of the molten mixtures was not observed. That is, only when EC is added to molten mixtures containing a polyglycerol fatty acid ester and theophylline, is the viscosity of the molten mixtures decreased.

When ethyl cellulose was added to a molten mixture containing a medicament other than theophylline, and a polymer other than ethyl cellulose was added to a molten mixture containing theophylline, a decrease in the viscosity was not observed.

EXAMPLES 13-18

Preparation of Core Particles

In view of the results of Test Example 1, the core particles of Example 13 were prepared as follows: 6750 g of triglycerol behenic acid half ester (hydroxyl value: 130, trade name: TR-HB) and 1800 g of glycerol monobehenic acid ester (hydroxyl value: 280, trade name: Poem B-100) were heated and fused, and 450 g of ethyl cellulose (7 cps, manufactured by Dow Chemical Company) and 6000 g of theophylline were mixed thereinto to give 15 kg of a molten mixture. This molten mixture was spray-cooled by a spray cooler equipped with a rotary disc having a diameter of 2.5 m (ODT-25, manufactured by Okawara Mfg Co., Ltd.) at an atomizer speed of 15000 rpm, and the particles thus obtained were screened with a 355 μm sieve, thereby giving theophylline-containing core particles with an average particle diameter of 130 μm.

Examples 14-18, the results of which are shown in Table 7, were conducted in the same manner as Example 13 to prepare similar core particles.

In all cases, the molten mixtures could be mixed efficiently, and theophylline-containing core particles in which ingredients were uniformly dispersed were obtained.

TABLE 7

|  | Ex. 13 | Ex. 14 | Ex. 15 | Ex. 16 | Ex. 17 | Ex. 18 |
| --- | --- | --- | --- | --- | --- | --- |
| Theophylline (%) | 40 | 40 | 40 | 40 | 40 | 40 |
| TR-HB (%) | 45 | 51 | 30 | 41 | 41 | 41 |
| B-100 (%) | 12 | 6 | 27 | 18 |  | 14 |
| P-100 (%) |  |  |  |  | 18 | 4 |
| EC (%) | 3 | 3 | 3 | 1 | 1 | 1 |
| Total (%) | 100 | 100 | 100 | 100 | 100 | 100 |

TEST EXAMPLE 2

Relationship Between Hydroxyl Value and Electrostatic Adhesion

Using particles of low-melting-point substances containing no pharmacologically active substances as core particles, the relationship between hydroxyl value and electrostatic adhesion of the core particles in fusion coating was investigated.

Particles of a low-melting-point substance (750 g) and talc (105 g) were charged into a jacketed high-shear mixer/granulator (vertical granulator, FM-VG-05, manufactured by Powrex Corporation) and agitated while heating at a jacket temperature of about 70° C. to carry out fusion coating. Once the fine powder of talc had disappeared, water was introduced into the jacket for cooling, thereby giving the fusion-coated particles of Reference Example 8.

For Reference Examples 9-11 and Comparative Reference Examples 1 and 2, fusion coating was conducted in the same manner as above. The extent of electrostatic adhesion of the core particles to the inner walls of the granulator is shown in Table 8.

Table 8 shows that in the fusion coating of Comparative Reference Examples 1 and 2 wherein the hydroxyl value of the particles is low, the electrostatic adhesion of the core particles to the inner walls of the granulator was extremely severe, resulting in a poor product yield, i.e., not giving the desired particles satisfactorily.

TABLE 8

|  | Ref. Ex. 8 | Ref. Ex. 9 | Comp. Ref. Ex. 1 | Comp. Ref. Ex. 2 | Ref. Ex. 10 | Ref. Ex. 11 |
| --- | --- | --- | --- | --- | --- | --- |
| Core particles | TR-2B | TB-82 | J-46B | DI-FB | Poem B-200 | TR-HB |
| Hydroxyl value | 190 | 70 | 15 | 18 | 190 | 132 |
| Terminal temperature of heating (° C.) | 68 | 68 | 67 | 68 | 65 | 68 |
| Extent of adhesion | minimal (±) | little (+) | severe (+++) | severe (+++) | minimal (±) | minimal (±) |

EXAMPLES 19-21

Fusion Coating: Talc Plus EC

In view of the results of Test Example 2, 750 g of the core particles obtained in Example 17, 18 g of ethyl cellulose (10 cps-FP, manufactured by Dow Chemical Company) and 162 g of talc were charged into a jacketed high-shear mixer/granulator (vertical granulator, FM-VG-05, manufactured by Powrex Corporation) and agitated while heating at a jacket temperature of about 70° C. to carry out fusion coating. Once the talc and EC had adhered to the core particles, the particles were cooled by reducing the jacket temperature, thereby giving fusion-coated particles. After adding and mixing light anhydrous silicic acid, the particles thus obtained were screened with a 355 μm sieve, thereby giving the sustained-release particles of Example 19.

For Examples 20 and 21, fusion coating was conducted in the same manner as above.

In the fusion coating of Examples 19-21, electrostatic adhesion of the core particles to the inner walls of the granulator did not occur at all, giving a product yield of about 99%.

TABLE 9

|  | Example | | |
| --- | --- | --- | --- |
|  | Ex. 19 | Ex. 20 | Ex. 21 |
| Core particles prepared in | Ex. 17 | Ex. 17 | Ex. 17 |
| Weight of core particles (g) | 750 | 750 | 750 |
| EC (10 cps-FP) (g) | 18 | 36 | 0 |
| Talc (g) | 162 | 144 | 180 |
| Light anhydrous silicic acid (g) | 1.5 | 1.5 | 1.5 |
| Total (g) | 931.5 | 931.5 | 931.5 |

EXAMPLES 22-32

Fusion Coating: Talc

Using the formulations shown in Tables 10 and 11, core particles (750 g) and talc were charged into a jacketed high-shear mixer/granulator (vertical granulator, FM-VG-05, manufactured by Powrex Corporation) and agitated while heating at a jacket temperature of about 70° C. to carry out fusion coating. Once the talc had adhered to the core particles, the particles were cooled by reducing the jacket temperature, thereby giving fusion-coated particles. After adding and mixing light anhydrous silicic acid, the particles thus obtained were screened with a 355 μm sieve, thereby giving sustained-release particles.

In the fusion coating of Examples 22-32, electrostatic adhesion of the core particles to the inner walls of the granulator did not occur at all, giving a product yield of about 99%.

In Tables 10 and 11, "talc (%)" refers to the weight % of talc coating relative to the weight of core particles.

TABLE 10

|  | Example | | | | |
| --- | --- | --- | --- | --- | --- |
|  | Ex. 22 | Ex. 23 | Ex. 24 | Ex. 25 | Ex. 26 |
| Core particles prepared in | Ex. 13 | Ex. 16 | Ex. 16 | Ex. 16 | Ex. 16 |
| Weight of core particles (g) | 750 | 750 | 750 | 750 | 750 |
| Talc (g) | 210 | 240 | 120 | 300 | 112.5 |
| Light anhydrous silicic acid (g) | 1.5 | 1.5 | 1.5 | 1.5 | 1.5 |
| Total weight (g) | 961.5 | 991.5 | 871.5 | 1051.5 | 864 |
| Talc (%) | 28% | 32% | 16% | 40% | 15% |

TABLE 11

|  | Example | | | | | |
| --- | --- | --- | --- | --- | --- | --- |
|  | Ex. 27 | Ex. 28 | Ex. 29 | Ex. 30 | Ex. 31 | Ex. 32 |
| Core particles prepared in | Ex. 14 | Ex. 16 | Ex. 14 | Ex. 15 | Ex. 16 | Ex. 16 |
| Weight of core particles (g) | 750 | 750 | 750 | 750 | 750 | 750 |
| Talc (g) | 120 | 150 | 150 | 270 | 112.5 | 187.5 |
| Light anhydrous silicic acid (g) | 1.5 | 1.5 | 1.5 | 1.5 | 1.5 | 1.5 |
| Total weight (g) | 871.5 | 901.5 | 901.5 | 1021.5 | 864 | 939 |
| Talc (%) | 16% | 20% | 20% | 36% | 15% | 25% |

EXAMPLES 33-36

Fusion Coating: Talc

Using the formulations shown in Table 12, core particles (750 g) and talc were charged into a jacketed high-shear mixer/granulator (vertical granulator, FM-VG-05, manufactured by Powrex Corporation) and agitated while heating at a jacket temperature of about 70° C. to carry out fusion coating. Once the talc had adhered to the core particles, the particles were cooled by reducing the jacket temperature, thereby giving fusion-coated particles. After adding and mixing light anhydrous silicic acid, the particles thus obtained were screened with a 355 μm sieve, thereby giving sustained-release particles.

In the fusion coating of Examples 33-36, electrostatic adhesion of the core particles to the inner walls of the granulator did not occur at all, giving a product yield of about 99%.

In Table 12, "talc (%)" refers to the weight % of talc coating relative to the weight of core particles.

TABLE 12

|  | Ex. 33 | Ex. 34 | Ex. 35 | Ex. 36 |
| --- | --- | --- | --- | --- |
| Core particles prepared in | Ex. 17 | Ex. 17 | Ex. 17 | Ex. 18 |
| Weight of core particles (g) | 750 | 750 | 750 | 750 |
| Talc (g) | 150 | 112.5 | 225 | 187.5 |
| Light anhydrous silicic acid (g) | 1.5 | 1.5 | 1.5 | 1.5 |
| Talc (%) | 20% | 15% | 30% | 25% |

COMPARATIVE EXAMPLE 17

Matrix Base Material Having a Low Hydroxyl Value

Triglycerol behenic acid full ester TR-FB (8400 g, hydroxyl value: 15) was heated and fused, mixed with 1200 g of EC and 6400 g of theophylline, and granulated by spray cooling, thereby giving core particles having an average particles diameter of 130 μm. These core particles (700 g) and talc (350 g) were mixed and charged into a jacketed high-shear mixer/granulator (vertical granulator, FM-VG-05, manufactured by Powrex Corporation) and agitated while heating at a jacket temperature of about 70° C. to carry out fusion coating.

During heating, talc, before thoroughly adhering to the core particles, was electrostatically adhered to the inner walls of the granulator. When heating and agitating were continued, the core particles were melted and adhered onto the inner walls, resulting in particles with incomplete fusion coating.

TEST EXAMPLE 3

A dissolution test was carried out using the fusion-coated particles obtained in Comparative Example 17.

This dissolution test was carried out according to *The Japanese Pharmacopoeia*, 14$^{th}$ Edition, Dissolution Test (2$^{nd}$ Method, Paddle Method). Test conditions included paddle stirring speed: 75 rpm, test solution: 900 ml 0.5% aqueous polysorbate 80 solution, and sample theophylline: a particulate pharmaceutical preparation corresponding to 100 mg theophylline. FIG. 1 shows the results.

As is clear from FIG. 1, the fusion-coated particles of Comparative Example 17 do not exhibit a controlled (sustained) theophylline release.

TEST EXAMPLE 4

Heat Treatment

Figure 2:
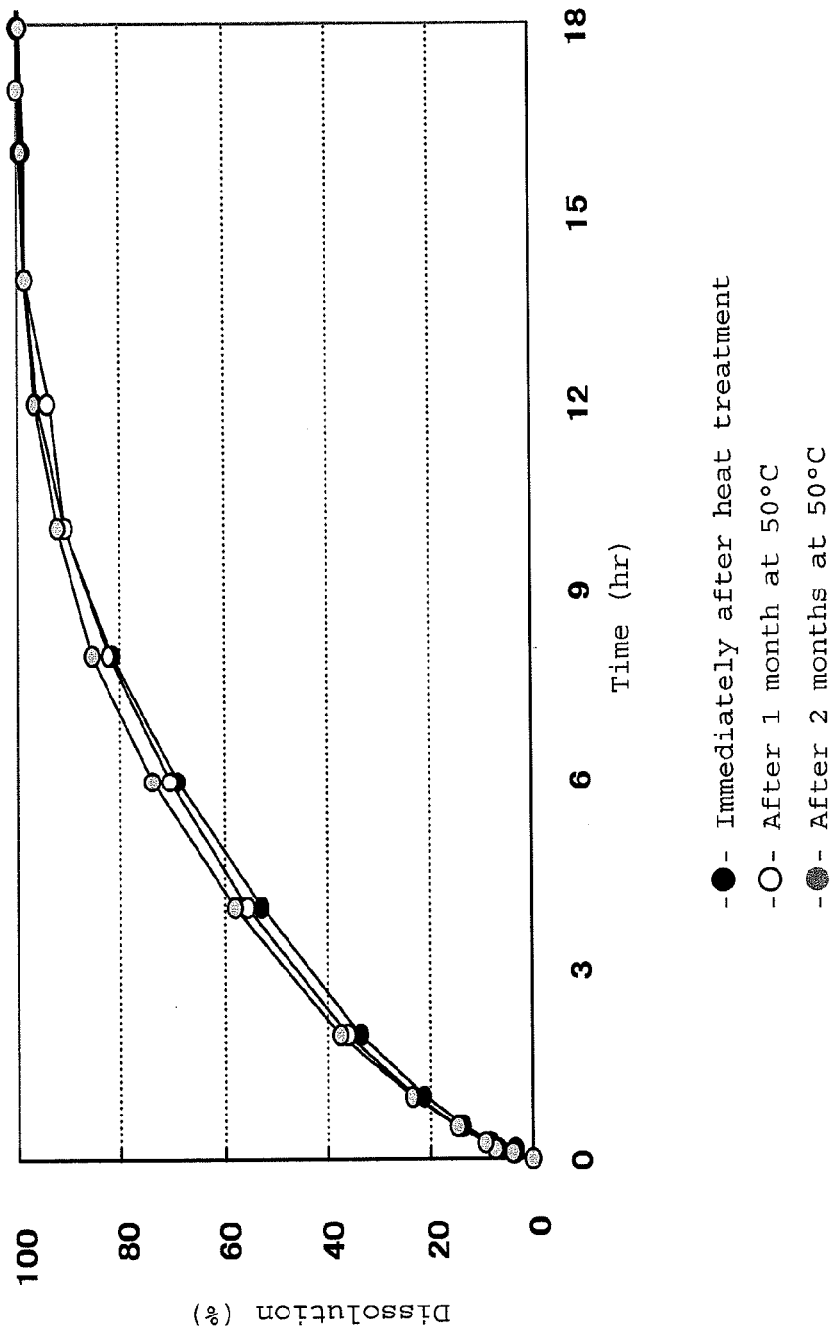
FIG. 2 is a graph showing the theophylline dissolution of the heat-treated fusion-coated particles of Example 28.

The fusion-coated particles obtained in Example 28 were subjected to a heat treatment at 50° C. for 12 hours, and then cooled to room temperature. These particles were filled into glass bottles and stored at 50° C. for 2 months. The results of dissolution tests conducted for the particles immediately after heat treatment (before storage), after 1-month storage and after 2-month storage show that the release rates for the particles before storage (after heat treatment) and after storage were not significantly different (see FIG. 2).

The aforementioned dissolution tests were conducted according to *The Japanese Pharmacopoeia*, 14$^{th}$ Edition, Dissolution Test (2$^{nd}$ Method, Paddle Method) under the same conditions as in Test Example 3.

Figure 3:
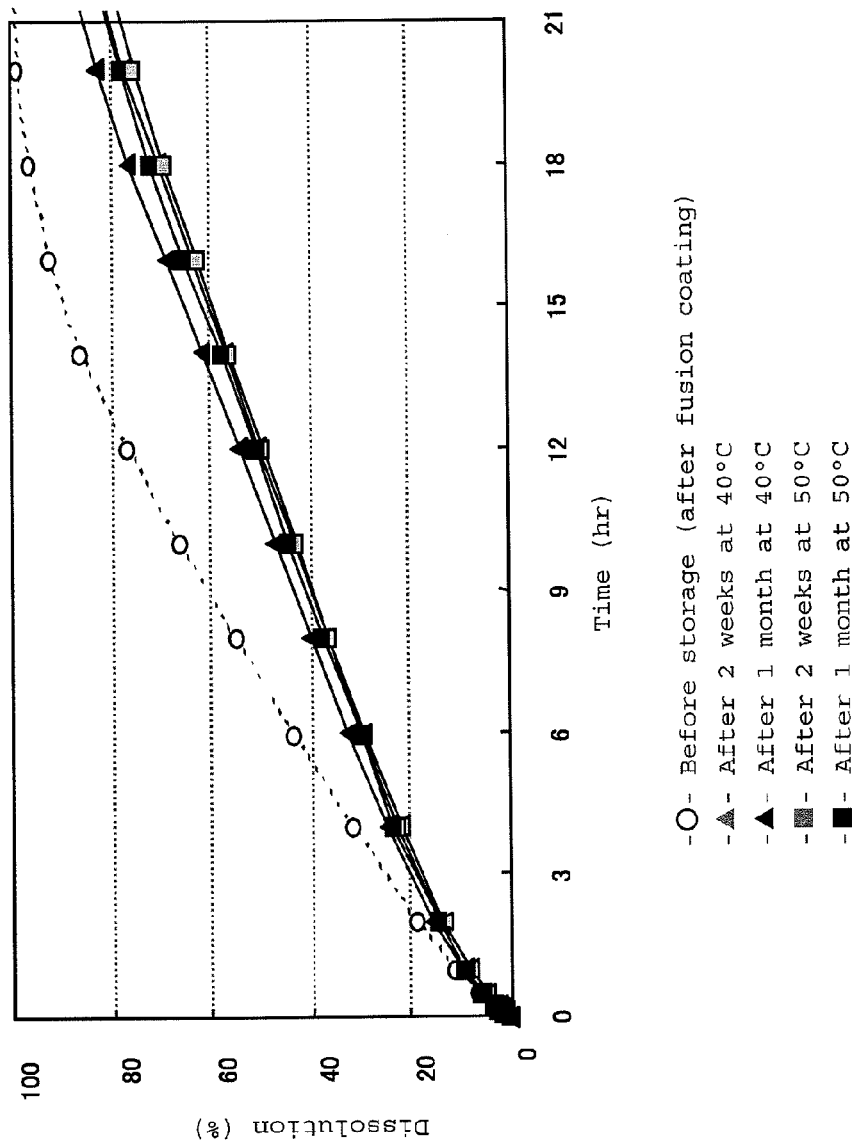
FIG. 3 is a graph showing the theophylline dissolution of the non-heat-treated fusion-coated particles of Example 25.

In contrast, the fusion-coated particles obtained in Example 25 without heat treatment were filled into glass bottles and stored at 40 or 50° C. The results of dissolution tests conducted as above for the particles after fusion coating (before storage), after 2-week storage and after 1-month storage demonstrate, as shown in FIG. 3, that the post-storage particles exhibit a decrease in dissolution rate compared with such particles before storage. This is presumably because the matrix base material of the fusion-coated particles undergoes crystalline transition during the storage.

Figure 4:
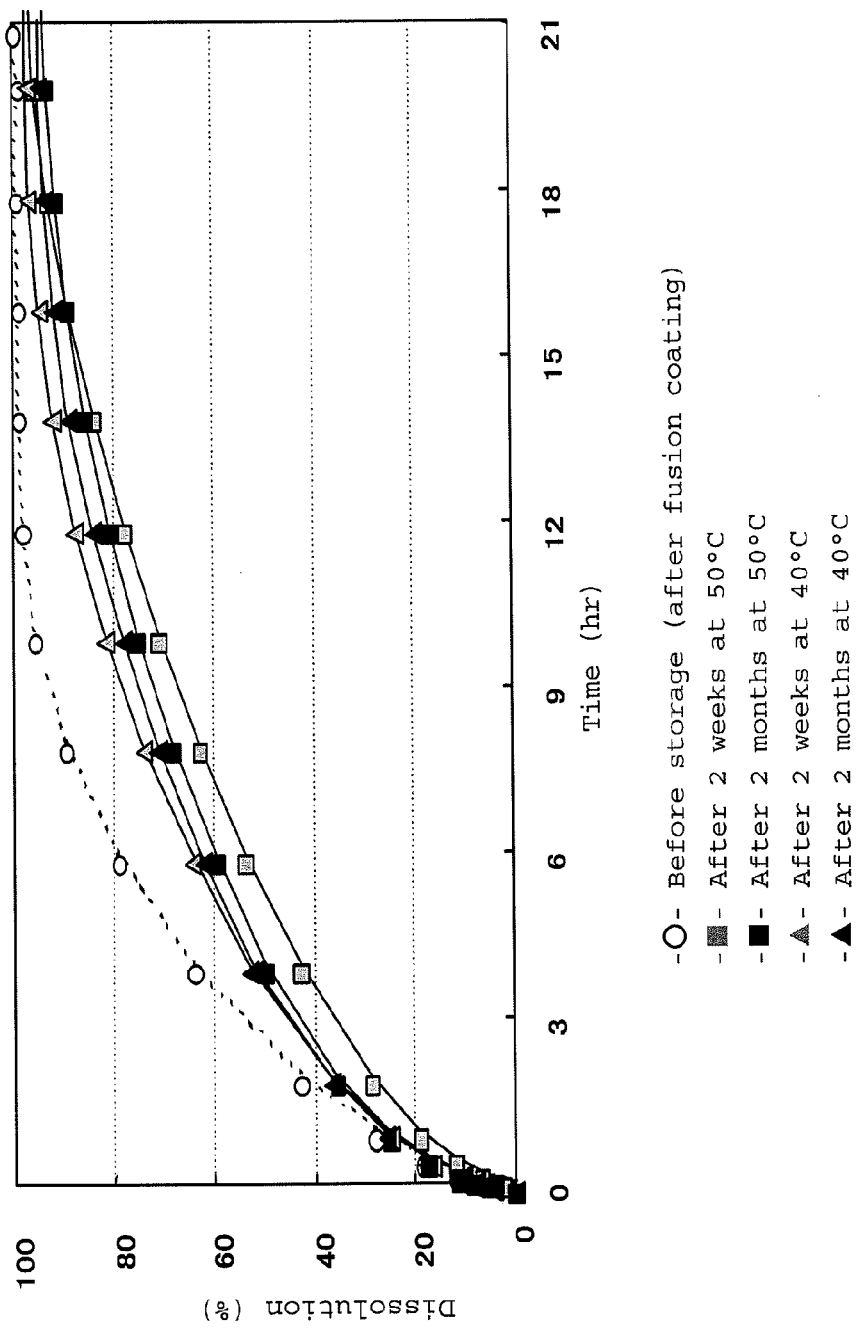
FIG. 4 is a graph showing the theophylline dissolution of the non-heat-treated fusion-coated particles of Example 28.

Furthermore, the fusion-coated particles obtained in Example 28 without heat treatment were filled into glass bottles and stored at 40 or 50° C. The results of dissolution tests conducted as above for the particles after fusion coating (before storage), after 2-week storage and after 2-month storage demonstrate, as shown in FIG. 4, that the post-storage particles exhibited a decrease in dissolution rate compared with the particles before storage. This is presumably because the matrix base material of the fusion-coated particles undergoes crystalline transition during the storage.

TEST EXAMPLE 5

Fusion Coating by Agitation Method and Fluid-Bed Method

The core particles obtained in Example 16 (800 g) and talc (160 g) were charged into a fluid-bed granulator (MP-01, manufactured by Powrex Corporation) to conduct fusion coating. Air was supplied at 75-90° C. to heat and fluidize. After the product was heated to 67° C., the air supply heater was turned off to gradually cool, thereby giving fusion-coated particles. When these particles were taken out, adhesion of fused matter to the meshed portion at the lower part of the container was observed, and there were many coarse particles. The recovered particles were screened with a 355 µm sieve and mixed with 1.5 g light anhydrous silicic acid to give the fluid-bed-fusion-coated particles of the present invention.

Figure 5:
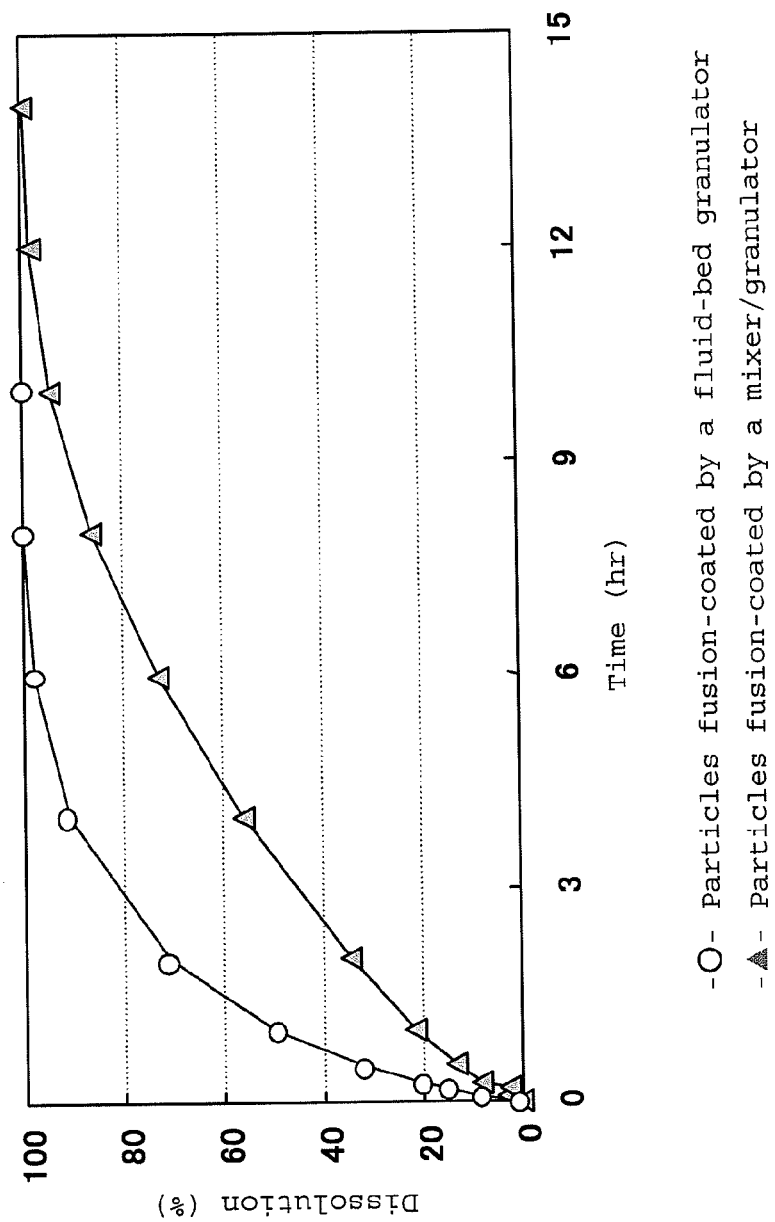
FIG. 5 is a graph comparing the theophylline dissolution of particles fusion-coated by an agitation method with the theophylline dissolution of particles fusion-coated by a fluid-bed method.

The particles of Example 28 fusion-coated by agitation method and the aforementioned particles fusion-coated by fluid-bed method were subjected to dissolution tests. Dissolution tests were conducted according to *The Japanese Pharmacopoeia*, 14$^{th}$ Edition, Dissolution Test (2$^{nd}$ Method, Paddle Method) under the same conditions in Test Example 3. FIG. 5 shows the results.

As shown in FIG. 5, the particles of Example 28 fusion-coated by agitation method, compared with the particles fusion-coated by fluid-bed method, exhibited a significantly-enhanced sustained theophylline release.

EXAMPLE 37

Dilution Process

The fusion-coated particles obtained in Example 27 (290.5 g), sucrose (100.5 g) and D-mannitol (70 g) were charged into a fluid-bed granulator (MP-01, manufactured by Powrex Corporation) for fluid-bed granulation using an aqueous sucrose solution as a binder solution. The particles thus obtained were dried, screened with a 850 µm sieve and mixed with 0.5 g light anhydrous silicic acid, thereby giving theophylline sustained release particles of the present invention.

EXAMPLE 38

Dilution Process

The fusion-coated particles obtained in Example 32 (313 g), sucrose (90 g) and D-mannitol (55 g) were charged into a fluid-bed granulator (MP-01, manufactured by Powrex Corporation) for fluid-bed granulation using an aqueous solution of 80 g sucrose and 2 g polysorbate 80 as a binder solution. The particles thus obtained were dried, screened with a 850 µm sieve and mixed with 0.5 g light anhydrous silicic acid, thereby giving theophylline sustained release particles of the present invention.

EXAMPLE 39

Dilution Process

The fusion-coated particles obtained in Example 28 (300.5 g), sucrose (95 g) and D-mannitol (63.5 g) were charged into a fluid-bed granulator (MP-01, manufactured by Powrex Corporation) for fluid-bed granulation using an aqueous solution of 120 g sucrose and 1.5 g polysorbate 80 as a binder solution. The particles thus obtained were dried, screened with a 850 µm sieve and mixed with 0.5 g light anhydrous silicic acid, thereby giving theophylline sustained release particles of the present invention.

EXAMPLE 40

Dilution Process

The fusion-coated particles obtained in Example 29 (300.5 g), sucrose (105 g) and D-mannitol (73.5 g) were charged into a fluid-bed granulator (MP-01, manufactured by Powrex Corporation) for fluid-bed granulation using an aqueous solution of 40 g sucrose and 1 g polysorbate 80 as a binder solution. The particles thus obtained were dried, screened with a 850 μm sieve and mixed with 0.5 g light anhydrous silicic acid, thereby giving theophylline sustained release particles of the present invention.

EXAMPLE 41

Dilution Process

The fusion-coated particles obtained in Example 31 (288 g), sucrose (101.5 g) and D-mannitol (80 g) were charged into a fluid-bed granulator (MP-01, manufactured by Powrex Corporation) for fluid-bed granulation using an aqueous solution of 30 g sucrose and 0.5 g sodium lauryl sulfate as a binder solution. The particles thus obtained were dried, screened with a 850 μm sieve and mixed with 0.5 g light anhydrous silicic acid, thereby giving theophylline sustained release particles of the present invention.

EXAMPLE 42

Dilution Process

The fusion-coated particles obtained in Example 33 (313 g), sucrose (100 g) and D-mannitol (81.5 g) were charged into a fluid-bed granulator (MP-01, manufactured by Powrex Corporation) for fluid-bed granulation using 4% aqueous hydroxypropyl cellulose solution as a binder solution. The particles thus obtained were dried, screened with a 850 μm sieve and mixed with 0.5 g light anhydrous silicic acid, thereby giving theophylline sustained release particles of the present invention.

All the references cited in this specification are incorporated herein by reference.

EFFECTS OF THE INVENTION

According to the method for preparing the theophylline sustained release particles of the present invention, by adding ethyl cellulose to a molten mixture of a polyglycerol fatty acid ester and theophylline, the viscosity of the molten mixture is decreased, thereby enhancing mixing efficiency.

Moreover, according to the method of the invention, the use of fusion coating performed by agitation enables the production of the desired fusion-coated particles in a high yield without having molten matter adhered on apparatus walls, unlike with fluid-bed fusion coating.

Furthermore, according to the method of the invention, fusion-coated particles may be subjected to a heat treatment to enhance and complete crystalline transition, enabling the production of a stable pharmaceutical preparation whose release rate does not changed over time.

The theophylline sustained release particles of the present invention obtained according to the aforementioned method are a homogenous matrix formulation in which theophylline is uniformly dispersed that has a superior sustained medicament releasability (dissolvability) and excellent storage stability. Moreover, it effectively masks the unpleasant taste of the medicament.

Furthermore, in the present invention, a matrix base material having a specific hydroxyl value is used. Therefore, when a fine powder is applied to core particles by fusion coating, the core particles are effectively prevented from electrostatically adhering to the inner walls of a mixer/granulator which may occur due to the matrix base material, enabling efficient production of a particulate pharmaceutical preparation having a sustained medicament release.

The invention claimed is:

1. A method for preparing medicament sustained release particles comprising applying a fine powder to core particles containing a pharmacologically active substance and a matrix base material that has a hydroxyl value of 60 or greater and contains a polyglycerol behenic acid ester by fusion coating while agitating, wherein the fine powder comprises at least one member selected from the group consisting of talc and ethyl cellulose.

2. The method according to claim 1 comprising
heating a pharmacologically active substance and a matrix base material that has a hydroxyl value of 60 or greater and contains a polyglycerol behenic acid ester to thereby give a liquefied mixture,
granulating the liquefied mixture by spray-cooling to obtain spherical core particles; and
applying the fine powder to the core particles by fusion coating.

3. The method according to claim 1, wherein the fusion coating is performed at a temperature in the vicinity of the melting point or the softening point of the matrix base material.

4. The method according to claim 1, wherein the matrix base material has a hydroxyl value of about 80 to about 350.

5. The method according to claim 1, further comprising a heat treatment step after the fusion coating.

6. The method according to claim 1, further comprising subjecting the core particles to a heat treatment before the fusion coating.

7. The method according to claim 5, wherein the heat treatment is conducted at a temperature from about 40° C. to about the melting point or the softening point of the matrix base material.

8. The method according to claim 1, wherein the polyglycerol behenic acid ester is a polyglycerol behenic acid half ester.

9. The method according to claim 1, wherein the polyglycerol behenic acid ester is a triglycerol behenic acid half ester.

10. Medicament sustained release particles obtainable by the method according to claim 5.

11. Medicament sustained release particles each comprising:
a core particle comprising a pharmacologically active substance and a matrix base material having a hydroxyl value of 60 or greater and containing a polyglycerol behenic acid ester, wherein the pharmacologically active substance is uniformly dispersed throughout the matrix base material, and
a coating layer comprising a fine powder and formed around the core particle by fusion coating using an agitation method,
wherein the medicament sustained release particles are heat-treated, and wherein the fine powder comprises at least one member selected from the group consisting of talc and ethyl cellulose.

12. The medicament sustained release particles according to claim 11, wherein the polyglycerol behenic acid ester is a polyglycerol behenic acid half ester.

* * * * *